United States Patent
Davies et al.

(10) Patent No.: US 7,529,685 B2
(45) Date of Patent: May 5, 2009

(54) SYSTEM, METHOD, AND APPARATUS FOR STORING, RETRIEVING, AND INTEGRATING CLINICAL, DIAGNOSTIC, GENOMIC, AND THERAPEUTIC DATA

(75) Inventors: Richard J. Davies, Saddle River, NJ (US); Rick Batye, Grayson, GA (US)

(73) Assignee: MD Datacor, Inc., Atlanta, GA (US)

( * ) Notice: Subject to any disclaimer, the term of this patent is extended or adjusted under 35 U.S.C. 154(b) by 1006 days.

(21) Appl. No.: 09/983,289

(22) Filed: Oct. 23, 2001

(65) Prior Publication Data

US 2003/0046114 A1    Mar. 6, 2003

Related U.S. Application Data

(60) Provisional application No. 60/315,020, filed on Aug. 28, 2001.

(51) Int. Cl.
*A61B 5/00* (2006.01)

(52) U.S. Cl. .................... 705/3; 707/5; 704/9

(58) Field of Classification Search ......... 705/2–3; 600/300; 704/9, 10; 707/104.1, 5
See application file for complete search history.

(56) References Cited

U.S. PATENT DOCUMENTS

| | | | | | |
|---|---|---|---|---|---|
| 5,853,989 | A | * | 12/1998 | Jeffreys et al. ............... | 435/6 |
| 5,948,058 | A | * | 9/1999 | Kudoh et al. ............... | 709/206 |
| 6,253,188 | B1 | * | 6/2001 | Witek et al. ............... | 705/14 |
| 6,303,297 | B1 | * | 10/2001 | Lincoln et al. ............. | 435/6 |
| 6,446,061 | B1 | * | 9/2002 | Doerre et al. ............... | 707/3 |
| 6,463,430 | B1 | * | 10/2002 | Brady et al. ............... | 707/3 |
| 6,484,166 | B1 | * | 11/2002 | Maynard ................... | 707/5 |
| 6,684,188 | B1 | * | 1/2004 | Mitchell et al. ............ | 705/3 |
| 6,704,729 | B1 | * | 3/2004 | Klein et al. ................ | 707/5 |
| 6,856,967 | B1 | * | 2/2005 | Woolston et al. ........... | 705/26 |

OTHER PUBLICATIONS

Lexicon Genetics Announces Database Agreement With Millennium Pharmaceuticals by (PR Newswire. New York: Oct. 5, 1999, p. 1; pp. 1-3).*
SEQUENOM and Gemini Identify Genes Linked to Cardiovascular Disease by (PR Newswire. New York: Nov. 28, 2000; p. 1; pp. 1-4).*
Susan Conway et al. "Unlocking Knowledge Assets" Knowledge Management Solutions From Microsoft, Chapter 6 (including Table of Contents); 2002 Microsoft Corporation; pp. i-ii, v-x, and 105-124.

* cited by examiner

*Primary Examiner*—Vanel Frenel
(74) *Attorney, Agent, or Firm*—Morris, Manning, Martin LLP

(57) ABSTRACT

A method, system, and computer program product for storing and retrieving patient data in a database connected to a network is disclosed. The method, system, and computer program product comprises storing clinical data in the database, extracting data from the clinical data, querying the database using a taxonomy that includes inclusive or exclusive search criterion, and receiving a result set. The method, system, and computer program product comprises creating a taxonomy that includes at least one search criterion, sending a query to the database, the query including said at least one search criteria, receiving the result set in response to the query, the result set including at least one result record, and displaying said at least one result record. The method, system, and computer program product can further include a user such as a clinical researcher, a treating physician, or a consulting physician analyzing the result set.

33 Claims, 39 Drawing Sheets

Figure 4A

```
 1  September 1, 2001
 2
 3  John Smith, MD
 4  123 Elm Street
 5  Suite 100
 6  City, ST   12345
 7
 8  RE:  Sue Jones
 9       0123456789
10
11  PROBLEM LIST:
12  1. Atrial fibrillation.
13  2. History of head and neck cancer.
14  3. Shortness of breath.
15  4. History of squamous cell carcinoma of the left hand.
16  5. On Coumadin anticoagulation.
17  6. Status post surgical reconstruction of left hand after
18     previous surgery for carcinoma.
19  7. Edema.
20
21  CURRENT MEDICATIONS:   Lanoxin 0.125 mg q.d., Coumadin 2 mg
22  q.d., Salagen 5 mg two t.i.d., Zocor 10 mg q.d., Diovan 80/
23  12.5 q.d., and multivitamins q.d.
24
25  ALLERGIES:   None known.
26
27  REASON FOR VISIT:   Follow-up for atrial fibrillation and
28  edema.
29
30  HISTORY OF PRESENT ILLNESS:   Dear Dr. Smith:
31
32  I saw Sue on 09/01/2001.  As you know she is an 80-year-old
33  woman with a history of atrial fibrillation.  She states that
34  she has been having some edema in her right leg.  She
35  previously complained of some discomfort and was referred for
36  noninvasive evaluation of her lower extremities as well as of
37  her carotids because of bruits.  She denies any recent chest
38  pain or significant palpitations.
```

Figure 4B

```
 1  September 1, 2001
 2  Sue Jones
 3  0123456789
 4
 5  PHYSICAL EXAMINATION:   Blood pressure 150/70, pulse 74 and
 6  irregular, respirations 16, and weight 117.  Afebrile.
 7  CHEST:  Clear to auscultation.
 8  CARDIOVASCULAR:  Irregularly irregular at 70 beats per minute.
 9  S1 and S2 are normal.  A 3/6 systolic ejection murmur.  No S3
10  gallop, click, or rub.  A2 was well preserved.
11
12  ABDOMEN:  Normal bowel sounds.
13  EXTREMITIES:  A trace pretibial edema is noted on the right,
14  none on the left.
15
16  DATA REVIEWED:  Noninvasive carotid study performed on
17  06/01/2001 demonstrates diffuse plaque bilaterally.  The
18  bruits noted are most likely due to lesion at the origin of
19  the external carotid.  The internal carotid arteries are
20  patent with no hemodynamically significant lesions.
21  Noninvasive study of the lower extremities demonstrated right
22  lower extremity with short segment distal superficial femoral
23  artery occlusion.  High-grade stenosis was noted in the left
24  distal popliteal artery involving the trifurcation.  Bilateral
25  calcific tibial arteries were noted.  Laboratory data drawn on
26  08/01/2001 revealed triglycerides of 144 with a cholesterol of
27  196 and HDL of 60 and LDL of 107.  Prothrombin time was 20.6
28  with an INR of 2.1.
29
30  ASSESSMENT:
31  1. Lower extremity discomfort.  The patient demonstrates
32     abnormality suggesting bilateral peripheral vascular
33     disease; however, her symptomatology is not classic for
34     claudication.  I suspect that his may be neuropathic or
35     possibly related to venous insufficiency with discomfort
36     from her edema.  We will refer for noninvasive venous
37     studies in light of the recurrent edema.
38  2. Hypertension.  The patient's blood pressure is reasonably
39     well controlled at this time.  Repeat blood pressure was
40     somewhat better at approximately 140/75.  We will continue
41     present medical regimen.
42  3. Hyperlipidemia, appears to be in good control.
43  4. Coumadin anticoagulation, appears adequate at this time on
44     present regimen.
```

Figure 4C

```
 1  September 1, 2001
 2  Sue Jones
 3  0123456789
 4
 5  PLAN:
 6  1. Continue present medical regimen.
 7  2. Noninvasive venous studies.
 8  3. Follow-up in two to three months, sooner p.r.n.
 9
10  John R. Able, M.D., F.A.C.C.
11
12  DD: 09/01/2001            MT: 111
13  DT: 09/04/2001            JOB: 666666/999999
```

Figure 5A

```
1  <?xml version="1.0" ?>
2      <Sections>
3          <SECTION compulsory="1">
4              <TITLE><![CDATA[REFERREDBY]]></TITLE>
5              <BODY><![CDATA[John Smith, MD
6  123 Street
7  Suite 123
8  City, ST  12345]]></BODY>
9              <FROM><![CDATA[Transcribed Text]]></FROM>
10         </SECTION>
11
12         <SECTION compulsory="1">
13             <TITLE><![CDATA[PROBLEM LIST]]></TITLE>
14             <BODY><![CDATA[1.  Atrial fibrillation.
15 2.  History of head and neck cancer.
16 3.  Shortness of breath.
17 4.  History of squamous cell carcinoma of the left hand.
18 5.  On Coumadin anticoagulation.
19 6.  Status post surgical reconstruction of left hand after
20 previous surgery for carcinoma.
21 7.  Edema.]]></BODY>
22             <FROM><![CDATA[Transcribed Text]]></FROM>
23         </SECTION>
24
25         <SECTION compulsory="1">
26             <TITLE><![CDATA[CURRENT MEDICATIONS]]></TITLE>
27             <BODY><![CDATA[Lanoxin 0.125 mg q.d., Coumadin 2
28 mg q.d., Salagen 5 mg two t.i.d., Zocor 10 mg q.d., Diovan 80/
29 12.5 q.d., and multivitamins q.d.]]></BODY>
30             <FROM><![CDATA[Transcribed Text]]></FROM>
31         </SECTION>
32
33         <SECTION compulsory="1">
34             <TITLE><![CDATA[ALLERGIES]]></TITLE>
35             <BODY><![CDATA[None known.]]></BODY>
36             <FROM><![CDATA[Transcribed Text]]></FROM>
37         </SECTION>
38
39         <SECTION compulsory="1">
40             <TITLE><![CDATA[REASON FOR VISIT]]></TITLE>
41             <BODY><![CDATA[Follow-up for atrial fibrillation
42 and edema.]]></BODY>
43             <FROM><![CDATA[Transcribed Text]]></FROM>
44         </SECTION>
45
```

Figure 5B

```
 1          <SECTION compulsory="1">
 2              <TITLE><![CDATA[HISTORY OF PRESENT ILLNESS]]></
 3 TITLE>
 4              <BODY><![CDATA[Dear Dr. Smith:
 5 I saw Sue on 09/01/2001.  As you know she is an 80-year-old
 6 woman with a history of atrial fibrillation.  She states that
 7 she has been having some edema in her right leg.  She
 8 previously complained of some discomfort and was referred for
 9 noninvasive evaluation of her lower extremities as well as of
10 her carotids because of bruits.  She denies any recent chest
11 pain or significant palpitations.]]></BODY>
12              <FROM><![CDATA[Transcribed Text]]></FROM>
13          </SECTION>
14
15          <SECTION compulsory="1">
16              <TITLE><![CDATA[PHYSICAL EXAMINATION]]></TITLE>
17              <BODY><![CDATA[Blood pressure 150/70, pulse 74 and
18 irregular, respirations 16, and weight 117.  Afebrile.
19 CHEST:  Clear to auscultation.
20 CARDIOVASCULAR:  Irregularly irregular at 70 beats per minute.
21 S1 and S2 are normal.  A 3/6 systolic ejection murmur.  No S3
22 gallop, click, or rub.  A2 was well preserved.
23 ABDOMEN:  Normal bowel sounds.
24 EXTREMITIES:  A trace pretibial edema is noted on the right,
25 none on the left..]]></BODY>
26              <FROM><![CDATA[Transcribed Text]]></FROM>
27          </SECTION>
28
29          <SECTION compulsory="1">
30              <TITLE><![CDATA[DATA REVIEWED]]></TITLE>
31              <BODY><![CDATA[Noninvasive carotid study performed
32 on 06/01/2001 demonstrates diffuse plaque bilaterally.  The
33 bruits noted are most likely due to lesion at the origin of
34 the external carotid.  The internal carotid arteries are
35 patent with no hemodynamically significant lesions.
36 Noninvasive study of the lower extremities demonstrated right
37 lower extremity with short segment distal superficial femoral
38 artery occlusion.  High-grade stenosis was noted in the left
39 distal popliteal artery involving the trifurcation.  Bilateral
40 calcific tibial arteries were noted.  Laboratory data drawn on
41 08/01/2001 revealed triglycerides of 144 with a cholesterol of
42 196 and HDL of 60 and LDL of 107.  Prothrombin time was 20.6
43 with an INR of 2.1.]]></BODY>
44              <FROM><![CDATA[Transcribed Text]]></FROM>
45          </SECTION>
```

Figure 5C

```
1          <SECTION compulsory="1">
2              <TITLE><![CDATA[ASSESSMENT]]></TITLE>
3              <BODY><![CDATA[1.  Lower extremity discomfort.
4  The patient demonstrates abnormality suggesting bilateral
5  peripheral vascular disease; however, her symptomatology is
6  not classic for claudication.  I suspect that his may be
7  neuropathic or possibly related to venous insufficiency with
8  discomfort from her edema.  We will refer for noninvasive
9  venous studies in light of the recurrent edema.
10 2.  Hypertension.  The patient's blood pressure is reasonably
11 well controlled at this time.  Repeat blood pressure was
12 somewhat better at approximately 140/75.  We will continue
13 present medical regimen.
14 3.  Hyperlipidemia, appears to be in good control.
15 4.  Coumadin anticoagulation, appears adequate at this time on
16 present regimen.]]></BODY>
17             <FROM><![CDATA[Transcribed Text]]></FROM>
18         </SECTION>
19
20         <SECTION compulsory="1">
21             <TITLE><![CDATA[PLAN]]></TITLE>
22             <BODY><![CDATA[1.  Continue present medical
23 regimen.
24 2.  Noninvasive venous studies.
25 3.  Follow-up in two to three months, sooner p.r.n. ]]></BODY>
26             <FROM><![CDATA[Transcribed Text]]></FROM>
27         </SECTION>
28
29         <SECTION compulsory="0">
30             <TITLE><![CDATA[CC_Count]]></TITLE>
31             <BODY><![CDATA[0]]></BODY>
32             <FROM><![CDATA[Computed by Return Handler]]><//
33 FROM>
34         </SECTION>
35
36         <SECTION compulsory="0">
37             <TITLE><![CDATA[CC_XML]]></TITLE>
38             <BODY>
39                <CC_XML></CC_XML>
40             </BODY>
41             <FROM><![CDATA[Computed by Return Handler]]><//
42 FROM>
43         </SECTION>
```

Figure 5D

```
1         <SECTION compulsory="0">
2             <TITLE><![CDATA[CharCount]]></TITLE>
3             <BODY><![CDATA[3333]]></BODY>
4             <FROM><![CDATA[Computed by Return Handler]]></
5  FROM>
6         </SECTION>
7
8         <SECTION compulsory="0">
9             <TITLE><![CDATA[FreeCC_Count]]></TITLE>
10            <BODY><![CDATA[0]]></BODY>
11            <FROM><![CDATA[Computed by Return Handler]]></
12 FROM>
13        </SECTION>
14
15        <SECTION compulsory="0">
16            <TITLE><![CDATA[RanAt]]></TITLE>
17            <BODY><![CDATA[09/04/2001 19:01:02]]></BODY>
18            <FROM><![CDATA[Computed by Return Handler]]></
19 FROM>
20        </SECTION>
21
22        <SECTION compulsory="0">
23            <TITLE><![CDATA[SMID_Count]]></TITLE>
24            <BODY><![CDATA[0]]></BODY>
25            <FROM><![CDATA[Computed by Return Handler]]></
26 FROM>
27        </SECTION>
28
29        <SECTION compulsory="0">
30            <TITLE><![CDATA[ACCESS_CODE]]></TITLE>
31            <BODY><![CDATA[4444]]></BODY>
32            <FROM><![CDATA[Database query]]></FROM>
33        </SECTION>
34
35        <SECTION compulsory="0">
36            <TITLE><![CDATA[AUDIOSECS]]></TITLE>
37            <BODY><![CDATA[222]]></BODY>
38            <FROM><![CDATA[Database query]]></FROM>
39        </SECTION>
```

Figure 5E

```
1       <SECTION compulsory="0">
2           <TITLE><![CDATA[DATEDICTATED]]></TITLE>
3           <BODY><![CDATA[09/01/2001]]></BODY>
4           <FROM><![CDATA[Database query]]></FROM>
5       </SECTION>
6
7       <SECTION compulsory="0">
8           <TITLE><![CDATA[DATETIMEDICTATED]]></TITLE>
9           <BODY><![CDATA[09/01/2001 04:01:02 PM]]></BODY>
10          <FROM><![CDATA[Database query]]></FROM>
11      </SECTION>
12
13      <SECTION compulsory="0">
14          <TITLE><![CDATA[DATETIMETRANSCRIBED]]></TITLE>
15          <BODY><![CDATA[09/04/2001 07:01:02 PM]]></BODY>
16          <FROM><![CDATA[Database query]]></FROM>
17      </SECTION>
18
19      <SECTION compulsory="0">
20          <TITLE><![CDATA[DATETRANSCRIBED]]></TITLE>
21          <BODY><![CDATA[09/04/2001]]></BODY>
22          <FROM><![CDATA[Database query]]></FROM>
23      </SECTION>
24
25      <SECTION compulsory="0">
26          <TITLE><![CDATA[DELIVERYMECHANISM]]></TITLE>
27          <BODY><![CDATA[1]]></BODY>
28          <FROM><![CDATA[Database query]]></FROM>
29      </SECTION>
30
31      <SECTION compulsory="0">
32          <TITLE><![CDATA[JOBDIR]]></TITLE>
33          <BODY><![CDATA[\\ATLFS01\DN3Live\submitted_jobs\
34 2001\09\13\16\17\666666]]></BODY>
35          <FROM><![CDATA[Database query]]></FROM>
36      </SECTION>
37
38      <SECTION compulsory="0">
39          <TITLE><![CDATA[JOB_GUID]]></TITLE>
40          <BODY><![CDATA[31655659-BDC5-4B7B-8410-
41 D0E1D309BC0F]]></BODY>
42          <FROM><![CDATA[Database query]]></FROM>
43      </SECTION>
```

Figure 5F

```
1     <SECTION compulsory="0">
2          <TITLE><![CDATA[JOB_ID]]></TITLE>
3          <BODY><![CDATA[666666]]></BODY>
4          <FROM><![CDATA[Database query]]></FROM>
5     </SECTION>
6
7     <SECTION compulsory="0">
8          <TITLE><![CDATA[MT_ID]]></TITLE>
9          <BODY><![CDATA[111]]></BODY>
10         <FROM><![CDATA[Database query]]></FROM>
11    </SECTION>
12
13    <SECTION compulsory="0">
14         <TITLE><![CDATA[MT_INITIALS]]></TITLE>
15         <BODY><![CDATA[#T]]></BODY>
16         <FROM><![CDATA[Database query]]></FROM>
17    </SECTION>
18
19    <SECTION compulsory="0">
20         <TITLE><![CDATA[ORG_ID]]></TITLE>
21         <BODY><![CDATA[5555]]></BODY>
22         <FROM><![CDATA[Database query]]></FROM>
23    </SECTION>
24
25    <SECTION compulsory="0">
26         <TITLE><![CDATA[ORIGINAL_JOB_NO]]></TITLE>
27         <BODY><![CDATA[99999]]></BODY>
28         <FROM><![CDATA[Database query]]></FROM>
29    </SECTION>
30
31    <SECTION compulsory="0">
32         <TITLE><![CDATA[ORIG_REPORT_NAME]]></TITLE>
33         <BODY><![CDATA[Followup Visit]]></BODY>
34         <FROM><![CDATA[Database query]]></FROM>
35    </SECTION>
36
37    <SECTION compulsory="0">
38         <TITLE><![CDATA[ORIG_WORKTYPE]]></TITLE>
39         <BODY><![CDATA[2]]></BODY>
40         <FROM><![CDATA[Database query]]></FROM>
41    </SECTION>
```

Figure 5G

```
1       <SECTION compulsory="0">
2           <TITLE><![CDATA[REPORT_ID]]></TITLE>
3           <BODY><![CDATA[65]]></BODY>
4           <FROM><![CDATA[Database query]]></FROM>
5       </SECTION>
6
7       <SECTION compulsory="0">
8           <TITLE><![CDATA[REPORT_NAME]]></TITLE>
9           <BODY><![CDATA[Letter]]></BODY>
10          <FROM><![CDATA[Database query]]></FROM>
11      </SECTION>
12
13      <SECTION compulsory="0">
14          <TITLE><![CDATA[USER_ACCOUNT_ID]]></TITLE>
15          <BODY><![CDATA[8888]]></BODY>
16          <FROM><![CDATA[Database query]]></FROM>
17      </SECTION>
18
19      <SECTION compulsory="0">
20          <TITLE><![CDATA[USER_CREDENTIALS]]></TITLE>
21          <BODY><![CDATA[M.D., F.A.C.C.]]></BODY>
22          <FROM><![CDATA[Database query]]></FROM>
23      </SECTION>
24
25      <SECTION compulsory="0">
26          <TITLE><![CDATA[USER_EMAIL]]></TITLE>
27          <BODY><![CDATA[infoserv@digitaldoctor.com]]></
28 BODY>
29          <FROM><![CDATA[Database query]]></FROM>
30      </SECTION>
31
32      <SECTION compulsory="0">
33          <TITLE><![CDATA[USER_FORENAME]]></TITLE>
34          <BODY><![CDATA[John R.]]></BODY>
35          <FROM><![CDATA[Database query]]></FROM>
36      </SECTION>
37
38      <SECTION compulsory="0">
39          <TITLE><![CDATA[USER_ID]]></TITLE>
40          <BODY><![CDATA[11111]]></BODY>
41          <FROM><![CDATA[Database query]]></FROM>
42      </SECTION>
```

Figure 5H

```
1     <SECTION compulsory="0">
2         <TITLE><![CDATA[USER_INITIALS]]></TITLE>
3         <BODY><![CDATA[JA]]></BODY>
4         <FROM><![CDATA[Database query]]></FROM>
5     </SECTION>
6
7     <SECTION compulsory="0">
8         <TITLE><![CDATA[USER_SIGNAME]]></TITLE>
9         <BODY><![CDATA[John R. Able, M.D., F.A.C.C.]]></
10 BODY>
11        <FROM><![CDATA[Database query]]></FROM>
12    </SECTION>
13
14    <SECTION compulsory="0">
15        <TITLE><![CDATA[USER_SURNAME]]></TITLE>
16        <BODY><![CDATA[Able]]></BODY>
17        <FROM><![CDATA[Database query]]></FROM>
18    </SECTION>
19
20    <SECTION compulsory="0">
21        <TITLE><![CDATA[WORKTYPE]]></TITLE>
22        <BODY><![CDATA[5]]></BODY>
23        <FROM><![CDATA[Database query]]></FROM>
24    </SECTION>
25
26    <SECTION compulsory="0">
27        <TITLE><![CDATA[ADT_ADMITDATE]]></TITLE>
28        <BODY><![CDATA[09/01/2001]]></BODY>
29        <FROM><![CDATA[ADT Feed]]></FROM>
30    </SECTION>
31
32    <SECTION compulsory="0">
33        <TITLE><![CDATA[ADT_FIRSTNAME]]></TITLE>
34        <BODY><![CDATA[Sue]]></BODY>
35        <FROM><![CDATA[ADT Feed]]></FROM>
36    </SECTION>
37
38    <SECTION compulsory="0">
39        <TITLE><![CDATA[ADT_FULLNAME]]></TITLE>
40        <BODY><![CDATA[JONES, SUE]]></BODY>
41        <FROM><![CDATA[ADT Feed]]></FROM>
42    </SECTION>
```

Figure 5I

```
1        <SECTION compulsory="0">
2            <TITLE><![CDATA[ADT_JOB_ID]]></TITLE>
3            <BODY><![CDATA[666666]]></BODY>
4            <FROM><![CDATA[ADT Feed]]></FROM>
5        </SECTION>
6
7        <SECTION compulsory="0">
8            <TITLE><![CDATA[ADT_LASTNAME]]></TITLE>
9            <BODY><![CDATA[Jones]]></BODY>
10           <FROM><![CDATA[ADT Feed]]></FROM>
11       </SECTION>
12
13       <SECTION compulsory="0">
14           <TITLE><![CDATA[ADT_PATIENTID]]></TITLE>
15           <BODY><![CDATA[0123456789]]></BODY>
16           <FROM><![CDATA[ADT Feed]]></FROM>
17       </SECTION>
18
19       <SECTION compulsory="0">
20           <TITLE><![CDATA[ADT_REC_ADT_INFO_PATIENT_ID]]></
21 TITLE>
22           <BODY><![CDATA[777777]]></BODY>
23           <FROM><![CDATA[ADT Feed]]></FROM>
24       </SECTION>
25
26       <SECTION compulsory="0">
27           <TITLE><![CDATA[ADT_REC_ADT_INFO_VISIT_ID]]></
28 TITLE>
29           <BODY><![CDATA[888888]]></BODY>
30           <FROM><![CDATA[ADT Feed]]></FROM>
31       </SECTION>
32
33       <SECTION compulsory="0">
34           <TITLE><![CDATA[ADT_SEARCH_KEY]]></TITLE>
35           <BODY><![CDATA[1]]></BODY>
36           <FROM><![CDATA[ADT Feed]]></FROM>
37       </SECTION>
38
39       <SECTION compulsory="0">
40           <TITLE><![CDATA[ADT_SEX]]></TITLE>
41           <BODY><![CDATA[F]]></BODY>
42           <FROM><![CDATA[ADT Feed]]></FROM>
43       </SECTION>
44
45    </Sections>
```

SYSTEM, METHOD, AND APPARATUS FOR STORING, RETRIEVING, AND INTEGRATING CLINICAL, DIAGNOSTIC, GENOMIC, AND THERAPEUTIC DATA

CROSS-REFERENCE TO A RELATED APPLICATION

This application hereby incorporates by reference the provisional application for letters patent, No. 60/315,020, titled "System, Method, and Apparatus for Storing, Retrieving, and Integrating Clinical, Diagnostic, Genomic, and Therapeutic Data", and filed in the United States Patent and Trademark Office on Aug. 28, 2001.

FIELD OF THE INVENTION

A method, system, and computer program product for storing and retrieving patient data in a database connected to a network is disclosed. In particular, the method, system, and computer program product comprises storing clinical data in the database, extracting data from the clinical data, querying the database using a taxonomy that includes inclusive or exclusive search criterion, and receiving a result set.

BACKGROUND OF THE INVENTION

The healthcare sector has the most stable growth rate of any sector of the U.S. economy. Furthermore, the demand for healthcare services typically increases proportionally to the age of the population. Since an average individual over age 65 consumes four-times more healthcare dollars than an average individual under age 65, the growth rate of the healthcare sector is likely to increase because the percentage of the U.S. population over age 65 will increase from 12% in 1992 to 18% in 2020.

A data warehouse is a collection of data designed to support clinical as well as patient management decision making. A data warehouse typically contains a wide variety of data that present a coherent picture of clinical or business conditions at a single point in time. Development of a data warehouse includes development of systems to extract data from operating systems and installation of a warehouse database system that provides clinicians or managers flexible access to the data. The term "data warehousing" generally refers to combining many different databases across an entire enterprise. In contrast, a "data mart" is a database, or collection of databases, designed to help clinicians and managers identify therapeutic strategies or make strategic, clinical, and business decisions about their patients. Whereas a data warehouse combines databases across an entire enterprise, data marts are usually smaller and focus on a particular subject or department. Some data marts, called dependent data marts, are subsets of larger data warehouses.

The vast accumulation of medical information and technology is opening doors for the discovery of new diagnostics, disease prevention strategies, and drug and device therapies for a host of diseases, including, but not limited to, cancer, heart disease, diabetes, hypertension, mental illness, allergic reaction, immune disorder, and infectious disease. Many diseases correlate to other specific contributory factors including genetic factors, family history, dietary issues, geographical locations, demographic data, and environmental factors. Thus, there is great interest in identifying these contributory factors to improve the accuracy of disease diagnosis and treatment. Moreover, since the future of healthcare will focus on disease prevention as well as past treatment and diagnosis, an important objective will be to identify individuals at risk for developing a disease.

One of the most powerful medical advances in recent years has been the increase in genetic information available to researchers and clinicians. Genomic studies will result in the development of a plethora of targeted therapies because researchers and clinicians will soon have the ability to profile variations in the Deoxyribonucleic Acid (DNA) of an individual and predict responses to a particular medicine. From the physician's perspective, identifying that a patient is likely to have a genetically based reaction to a drug will be of paramount importance. Approximately 7% of all patients have severe adverse reactions to prescribed medications, with drug side effects being the 5th leading cause of death in the United States in 1997 (Pharmacogenomics-Offering a Wealth of Targets for the Pharma Prospector; IMS Health Web Site). Thus, a need exists for clinical intelligence to enable a physician to prospectively identify when a clinical profile, family history, or symptom for a patient suggests a genetically based reaction to a particular therapy. A patient identified in this manner will be a candidate for genetic screening to definitely determine whether they have the genetic anomaly that will cause an adverse side effect. A physician will be able to use this information to prescribe more effective medicines and treatments.

In addition to identifying therapeutic strategies, the healthcare industry recognizes that a database system containing electronic medical records (EMRs) would improve patient care and increase the operational efficiency of the physician's practice. An efficient EMR system would provide valuable information for a broad range of applications, including but not limited to, diagnostic, therapeutic, marketing research (i.e., passive recruitment of a research population), clinical trial recruitment, and marketing services (i.e., active recruitment of a research population). Even though EMR companies have developed EMR systems and marketed the benefit of the EMR for more than a decade, adoption of the technology has been slow because integration of those systems requires not only monetary cost, but also workflow modifications. Thus, automation in most physicians' practices is limited to small-scale client-server based billing and scheduling applications. Very few physician practices have EMR software or other database management capability, and fewer still have information technology (IT) support. Yet there is a growing need for EMR management because of the increasingly complex regulatory environment facing clinicians. Remaining compliant with new healthcare regulations and practice guidelines is nearly impossible with a paper-based system. Moreover, PCT patent application serial number WO 00/51053 refers to a clinical and diagnostic database that contains patient records including phenotype, genotype, and sample information for the patient. The database system described in that PCT application, however, relies primarily upon genotype or stored sample information to generate correlations between phenotype and genotype.

Moreover, the medical database in the prior art force a physician to modify the normal process for collecting information because those databases rely on a physician to complete a questionnaire or involve other specific restrictions on data entry that are inconvenient and undesirable for the physician. Exemplary medical databases in the prior art include the epidemiological database disclosed in U.S. Pat. Ser. No. 5,911,132, and the MedLEE information extraction system disclosed in U.S. Pat. Ser. No. 6,182,029. Thus, there is a need for a database system that can generate information concerning either a disease risk or a susceptibility type, or drug response polymorphisms without requiring clinicians to change individual practice behavior.

A successful product or service in the healthcare industry will benefit the quality of life for a large number of patients by focusing on the physician's tasks and presenting a cost-effective solution to a recognized problem. A healthcare industry product and service that automates the collection and processing of clinical documentation by a physician will also provide clinical and economic value to the patient's medical record.

FIG. 1 illustrates the prior art clinical documentation process. The process begins when patient 100 visits physician 110 for a clinical reason. The visit can be in any clinical setting such as a private office, a health clinic, or a hospital and for any clinical reason such as an annual physical or to remedy of a specific medical ailment. As a result of the visit, physician 110 compiles a clinical note that may include historic medical information, vital signs, symptomatic descriptions, pharmaceutical prescriptions, or diagnostic conclusions. Following the visit, physician 110 connects to transcription service 130 using public switched telephone network (PSTN) 120 to dictate the clinical note for patient 100. Transcription service 130 stores the dictated clinical note in an audio format on storage device 131. Transcriptionist 132 retrieves the dictated clinical note from storage device 131, transcribes the note into electronic medical record 135, and stores electronic medical record 135 in a digital format on storage device 131. Physician 110 reviews electronic medical record 135 and stores a printed copy of electronic medical record 135 in paper based charting 140 associated with patient 100.

Following the visit with patient 100, physician 110 may recommend that clinical provider 115 perform a clinical test on patient 100. Physician 110 receives the results of the clinical test, reviews the results, discusses the results with patient 100, and stores the results in paper based charting 140 associated with patient 100.

The prior art clinical documentation process shown in FIG. 1 lacks the ability to efficiently search for data that is not known to be associated with a specific patient. Thus, there is a need for a system, method, and apparatus that automates the clinical documentation process and provides for storage and retrieval of clinical, diagnostic, and treatment data input in a natural human language format. The system, method, and apparatus will provide software tools to define disease or clinical term taxonomies that group the parsed data and define search criteria to enable intelligent searching of the data warehouse. The system, method, and apparatus disclosed herein automates the clinical documentation process and provides an engine and search tools for a data warehouse that unlocks the clinical and economic value of patient medical records.

SUMMARY OF THE INVENTION

A method, system, and computer program product for retrieving a result set from a database that includes data is disclosed. The method, system, and computer program product comprises creating a taxonomy that includes at least one search criterion, sending a query to the database, the query including said at least one search criteria, receiving the result set in response to the query, the result set including at least one result record, and displaying said at least one result record. The method, system, and computer program product can further comprise a user such as a clinical researcher, a treating physician, or a consulting physician analyzing the result set.

The creating of the taxonomy can further include adding at least one search rule to the taxonomy that includes at least one search characteristic, storing the taxonomy, and validating the taxonomy. Each search rule includes an inclusion search rule to define at least one inclusion search characteristic, wherein running the inclusion rule against the database generates at least one inclusion result record, each inclusion result record including said at least one inclusion search characteristic. Alternatively, each search rule includes an exclusion rule to define at least one exclusion search characteristic, wherein running the exclusion rule against the database generates at least one exclusion result record, each exclusion result record excluding said at least one exclusion search characteristic. Alternatively, each search rule includes an inclusion rule to define at least one inclusion search characteristic and an exclusion rule to define at least one exclusion search characteristic, wherein running the inclusion rule against the database generates at least one inclusion result record, each inclusion result record including said at least one inclusion search characteristic and wherein running the exclusion rule against the database generates at least one exclusion result record, each exclusion result record excluding said at least one exclusion search characteristic. In either case, the search characteristic includes an illness, a drug prescription, a medical coverage plan, family history data, demographic data for the patient, a specialty for a physician, or a clinical diagnosis phrase. The demographic data including a geographic location, a gender, or an age. The clinical diagnosis phrase including a myocardial infarction, an LDL, a heart attack, or a bundle branch block.

The validating of the taxonomy can further include running the taxonomy against the database, receiving the result set, and displaying the result set. The running of the taxonomy can further include notifying the database to run the taxonomy. The receiving of the result set can further include receiving an inclusion result set, wherein said at least one search rule includes an inclusion rule and running the inclusion rule against the database generates the inclusion result set, each record in the inclusion result set including at least one inclusion search characteristic. Alternatively, the receiving of the result set can further include receiving an exclusion result set, wherein said at least one search rule includes an exclusion rule and running the exclusion rule against the database generates the exclusion result set, each record in the exclusion result set including at least one exclusion search characteristic. Alternatively, the receiving of the result set can further include receiving an inclusion result set, wherein said at least one search rule includes an inclusion rule and running the inclusion rule against the database generates the inclusion result set, each record in the inclusion result set including at least one inclusion search characteristic and receiving an exclusion result set, wherein said at least one search rule includes an exclusion rule and running the exclusion rule against the database generates the exclusion result set, each record in the exclusion result set including at least one exclusion search characteristic, wherein each record in the exclusion result set is flagged.

The creating of the taxonomy can further include analyzing the result set and updating the taxonomy based on the analyzing of the result set. The updating of the taxonomy can further include unflagging an excluded record or flagging an included record.

In one embodiment, the analyzing of the result set can determine a disease risk or susceptibility type for at least one patient. Genetic testing of said at least one patient could detect a disease such as cancer, include germ-line testing, or identify at least one modifier gene. Somatic testing of said at least one patient could test a sample such as a tissue sample or a tumor sample to detect the disease, predict a drug response, or yield prognostic information about the disease or a propensity for the disease. Proteonomic testing of said at least one patient could yield prognostic information about the disease or a propensity for the disease. In another embodiment, the analyzing of the result set can identify at least one patient including a characteristic such as a drug reaction polymorphism, a hypertension drug response polymorphism, or a characteristic that is necessary for said at least one patient to be eligible for a clinical trial. In another embodiment, the result set generates a treatment suggestion for at least one patient, identifies at least one clinical trial for which said at least one patient is eligible, models a virtual clinical trial protocol, or generates market research data or market services data.

In one embodiment, the data is diagnostic data that includes past diagnosis and treatment data, medical history data, biochemical data, physiologic data, proteonomic data, family history data, dietary data, exercise data, demographic data, or drug response history data. The data also may include genotype data or haplotype data such as a chromosome structure, a DNA sequence, a length of a specific gene or region, a gene expression, or at least one single nucleotide polymorphism (SNP). In another embodiment, the data is related to a genetic-based disease and includes oncology data, urology data, cardiology data, gastroenterology data, orthopedic data, immunology data, rheumatology data, neurology data, pulmonology data, internal medicine data, family practice medicine data, and demographic data. In another embodiment, the database is a data warehouse that may include an archive database, an error log, or an audit log.

A method, system, and computer program product for storing data for a patient in a database connected to a network is disclosed. The method, system, and computer program product comprises receiving clinical data for the patient, storing the clinical data in an archive database connected to the network, extracting data from the clinical data, and storing the data in the database. The method, system, and computer program product can further include storing the structured file in the database. Alternatively, the method, system, and computer program product can further include creating a record in the database for the patient and populating the record with the data.

The receiving of the clinical data can further include establishing a network connection to a server computer that includes the clinical data and requesting the clinical data from the server computer. The receiving of the clinical data also can include destroying the network connection to the server computer after successfully receiving the clinical data.

The extracting of the data can further include creating a structured file, parsing the clinical data, and copying the clinical data into the structured file. The clinical data including at least one data segment and the structured file including a tag for each data segment in said at least one data segment. The parsing of the clinical data can further include locating at least one data segment in the clinical data. In addition, the parsing of the clinical data can include converting the data in said at least one data segment to another data format to improve the performance of the database when performing a search, a record addition, or a record deletion. Alternatively, the parsing of the clinical data can include linking the data in said at least one data segment to related clinical data for another patient. Alternatively, the parsing of the clinical data can include recognizing a known error in the clinical data, wherein the parsing of the clinical data corrects the known error prior to the copying of the clinical data. Alternatively, the parsing of the clinical data can include storing an unknown error in an error database. In another embodiment, the tag in the structured file is an extensible markup language tag, a hypertext markup language tag, a simple generalized markup language tag, or a health level seven tag.

In one embodiment, the data is diagnostic data that includes past diagnosis and treatment data, medical history data, biochemical data, physiologic data, proteonomic data, family history data, dietary data, exercise data, demographic data, or drug response history data. The data also may include genotype data or haplotype data such as a chromosome structure, a DNA sequence, a length of a specific gene or region, a gene expression, or at least one single nucleotide polymorphism (SNP). In another embodiment, the clinical data is an electronic medical record including a clinical note dictated by a physician, a laboratory report, or a laboratory result. In yet another embodiment, the data is related to a genetic-based disease and includes oncology data, urology data, cardiology data, gastroenterology data, orthopedic data, immunology data, rheumatology data, neurology data, pulmonology data, internal medicine data, family practice medicine data, and demographic data. In another embodiment, the database is a data warehouse that may include an archive database, an error log, or an audit log.

In another embodiment, the system, method, and apparatus for storing and retrieving clinical, diagnostic, and treatment data. The system, method, and apparatus parses a transcriptional data feed, electronic medical record, or an historical third-party database, stores the parsed data in a data warehouse, and provides software tools to define disease or clinical taxonomies that group the parsed data and define search criteria to enable intelligent searching of the data warehouse.

The present invention relates to a general-purpose computer system, method, and apparatus including a database that contains information useful for clinical, diagnostic, and other purposes. In particular, the system allows a user to input clinical information for a patient from any source, including the physician's dictated notes, laboratory reports, EKG or other instrument report, CAT scan, X-ray, functional or imaging studies, or any test that generates a result in an electronic-based medium to create a patient record in the form of an electronic medical record, and correlates the patient clinical information from the electronic medical record with other patient records or information in the data warehouse. The system further enables users to obtain suggestions for diagnostic, genetic testing, and/or treatment. The present invention also relates to methods of extracting and storing clinical information, and provides methods for searching and correlating the information, and identifying patient populations that share common attributes.

The present invention further relates to a general-purpose computer system, method, and apparatus that includes a database containing a plurality of electronic medical records, each record containing clinical information for an individual patient including, for example, phenotype, medical, family, biochemical, physiologic, proteonomic, geographic, diet, exercise, demographic, and drug response history. The present invention further relates to a system which includes genotype and/or haplotype information. The electronic medical records and methods disclosed herein are useful for a broad range of applications, including, but not limited to, clinical, diagnostic, market research, clinical trial, and marketing services applications.

The present invention further relates to a method for determining a patient's disease risk and susceptibility type comprising extracting clinical information from any relevant clinical source to create an electronic medical record, correlating the patient's clinical information with information from the system and/or accessed from one or more public or private domain databases, and generating a result set that includes a suggestion for genetic, proteonomic, and/or other type of diagnostic testing.

The present invention also relates to displaying the identified correlation, and/or calculating the statistical significance of the identified correlation.

The present invention further relates to entering the results of the genetic, proteonomic, and/or other diagnostic test or transmission into the data warehouse system, and generating a result set that includes a suggestion for treatment based upon the patient's record.

The present invention also relates to a method for identifying a patient with a drug response polymorphism comprising creating an electronic medical record by extracting the patient's clinical information including drug reaction information from any relevant source, correlating the patients information with information in the system and/or accessed from one or more public or private domain databases relating to single polynucleotide polymorphisms (SNPs), and generating a result set that includes a suggestion for genetic testing of possible SNPs identified to be correlated with the drug response.

The present invention further relates to the step of entering the result of the genetic test into the system, after which the system generates a suggestion for an alternative drug therapy based upon the patient's record.

The present invention also relates to a method for identifying a subject for a clinical trial comprising extracting clinical information to create an electronic medical record, correlating the patient's clinical information with other patient records in the system, identifying a population, or sub-population of patients having similar phenotypes, genotypes, or clinical characteristics, and identifying clinical trials which would be appropriate for the patient's participation.

The present invention further relates to the general-purpose computer system, method, and apparatus described herein as applied to a broad variety of disease categories including, but not limited to, cancer, heart disease, diabetes, hypertension, mental illness, allergies, infectious, neurological and immunological diseases.

BRIEF DESCRIPTION OF THE DRAWINGS

The accompanying figures best illustrate the details of the system, method, and apparatus for storing and retrieving clinical, diagnostic, and treatment data, both as to its structure and operation. Like reference numbers and designations in the accompanying figures refer to like elements.

FIGS. 4A through 4C depict an exemplary electronic medical record for a fictitious patient.

FIGS. 5A through 5I depict the exemplary electronic medical record shown in FIGS. 4A through 4C as an exemplary structured electronic medical record including XML field tagging.

DETAILED DESCRIPTION OF THE INVENTION

Figure 1:
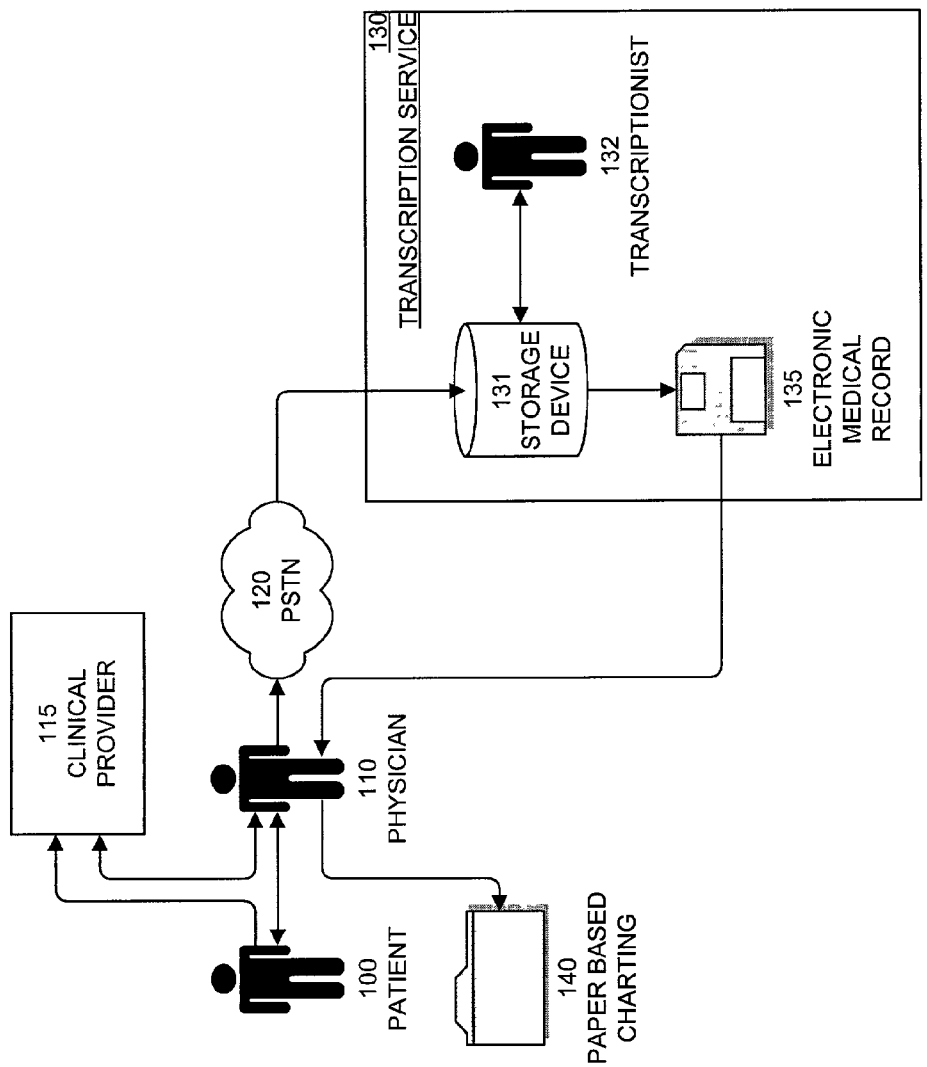
FIG. 1 illustrates the prior art clinical documentation process.
Figure 2:
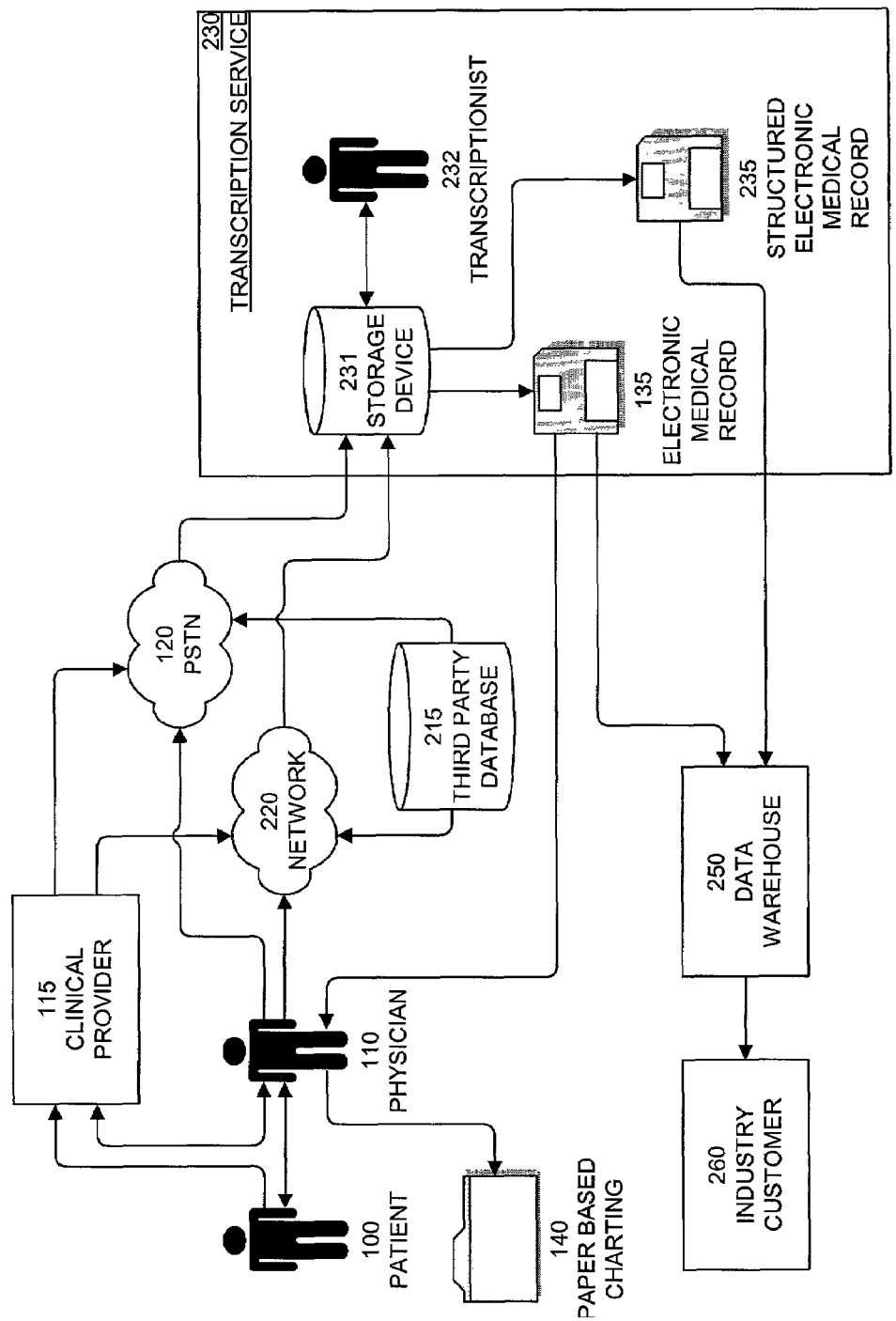
FIG. 2 illustrates an embodiment of a system that integrates a data warehouse for storing and retrieving clinical, diagnostic, and treatment data into the prior art clinical documentation process shown in FIG. 1.

FIG. 2 illustrates an embodiment of a system that integrates a data warehouse for storing and retrieving clinical, diagnostic, and treatment data into the prior art clinical documentation process shown in FIG. 1. In another embodiment, the system integrates a data warehouse into the prior art clinical documentation process to determine a disease risk or susceptibility type for a patient. In any embodiment, the prior art clinical documentation process remains in tact in the system shown in FIG. 2 and includes additional features to address the shortcomings in the prior art process.

In FIG. 2, physician 110 can connect with transcription service 230 using either public switched telephone network (PSTN) 120 or network 220. PSTN 120 includes traditional landline telephone networks, mobile or cellular telephone networks, and satellite-based telephone networks. Network 220 includes the public Internet, wide area networks, or local area networks using a transmission protocol such as transmission control protocol/Internet protocol (TCP/IP) or file transfer protocol (FTP), or personal area networks such as a Bluetooth network. Physician 110 may input clinical, diagnostic, and treatment data into the system shown in FIG. 2 using a variety of audio or digital input formats. The audio input formats include traditional audio over a PSTN as well as cellular, satellite, and digital audio over a wireless network. The digital input formats include voice recognition technology, digital audio, digital audio/video, digital documents such as word processing documents and portable data format (PDF) documents, and digital image files.

In addition to receiving input from physician 110 or clinical provider 115, the system shown in FIG. 2 may receive input from third party database 215. Third party database 215 includes pharmacogenomics, laboratory, and instrumentation databases and other publicly available medical databases. Furthermore, third party database 215 communicates with the system shown in FIG. 2 via PSTN 120 or network 220. Using a communications protocol such as transmission control protocol/Internet protocol (TCP/IP) or file transfer protocol (FTP), the system shown in FIG. 2 retrieves the appropriate information.

In FIG. 2, since physician 110 may input data in a variety of formats, storage device 231 of transcription service 230 stores not only audio input formats, but also digital input formats. The system transcribes the input data from physician 110 into electronic medical record 135 and forwards the record to physician 110 via either PSTN 120 or network 220. Transcription service 230 also transcribes the input data from physician 110 into structured electronic medical record 235. Structured electronic medical record 235 augments the contents of electronic medical record 135 by segmenting the record into fields and associating a "tag" with each field. The field tagging may use a technology such as the Extensible Markup Language (XML), a tagging system based on the hypertext markup language (HTML) and the simple generalized markup language (SGML), or Health Level Seven (HL7), a healthcare industry tagging standard. A subset of the functions performed by transcription service 230 may be performed, either alone or in combination, by the Speech Machines™ DictationNet service offering, as well as similar service offerings by Vianeta™, MedRemote™, and Total eMed™. FIGS. 4A through 4C depict an exemplary electronic medical record for a fictitious patient. FIGS. 5A through 5I depict the exemplary electronic medical record shown in FIGS. 4A through 4C as an exemplary structured electronic medical record including XML field tagging.

FIG. 2 also illustrates the interactions between transcription service 230, data warehouse 250, and industry customer 260. Data warehouse 250 receives, as input data, electronic medical record 135 and structured electronic medical record 235 from transcription service 230. Data warehouse 250 stores the input data in a database and provides search tools that industry customer 260 may use to search through the data in data warehouse 250. Industry customer 260 includes physician 110, medical marketing agencies, medical device manufacturers, Medicare, clinical research organizations, and companies focused on pharmacology, genetics, genomics, pharmacogenomics, or bio-technology.

Figure 3:
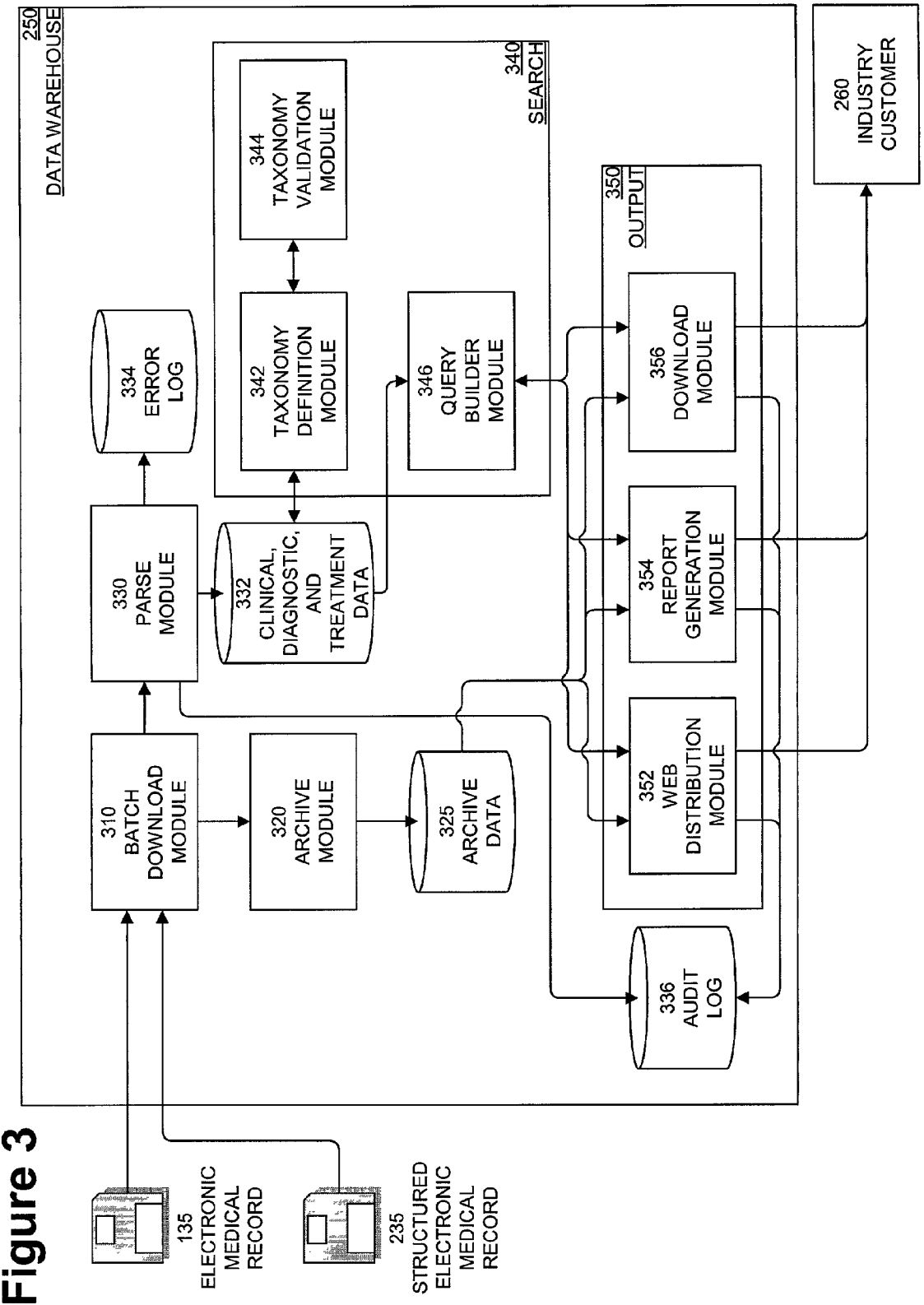
FIG. 3 illustrates the modules that comprise data warehouse 250 shown in FIG. 2.

FIG. 3 illustrates, in greater detail, the modules that comprise data warehouse 250 shown in FIG. 2. Batch download module 310 receives input data for data warehouse 250 from electronic medical record 135 and structured electronic medical record 235. Archive module 320 stores a backup or archival copy of the input data in archive data 325. Parse module 330 processes the input data and stores result data in clinical, diagnostic, and treatment data 332, error log 334, and audit log 336. Search 340 includes taxonomy definition module 342, taxonomy validation module 344, and query builder 346 to perform search functions on clinical, diagnostic, and treatment data 332 and produce query results for output 350. Output 350 includes web distribution module 352, report generation module 354, and download module 356 to distribute query results from search 340 to industry customer 260. Web distribution module 352, report generation module 354, and download module 356 also store result data in audit log 336.

Archive data 325, clinical, diagnostic, and treatment data 332, error log 334, and audit log 336 are shown in FIG. 2 as independent databases, however, the present invention contemplates consolidating these databases as well as distributing the databases to suit efficiency and performance requirements. In one embodiment, these databases use a relational database management system such as the Oracle 8i product (version 8.1.7) by Oracle™. Another embodiment of these databases may use an object-oriented database management system architecture.

Figure 6:
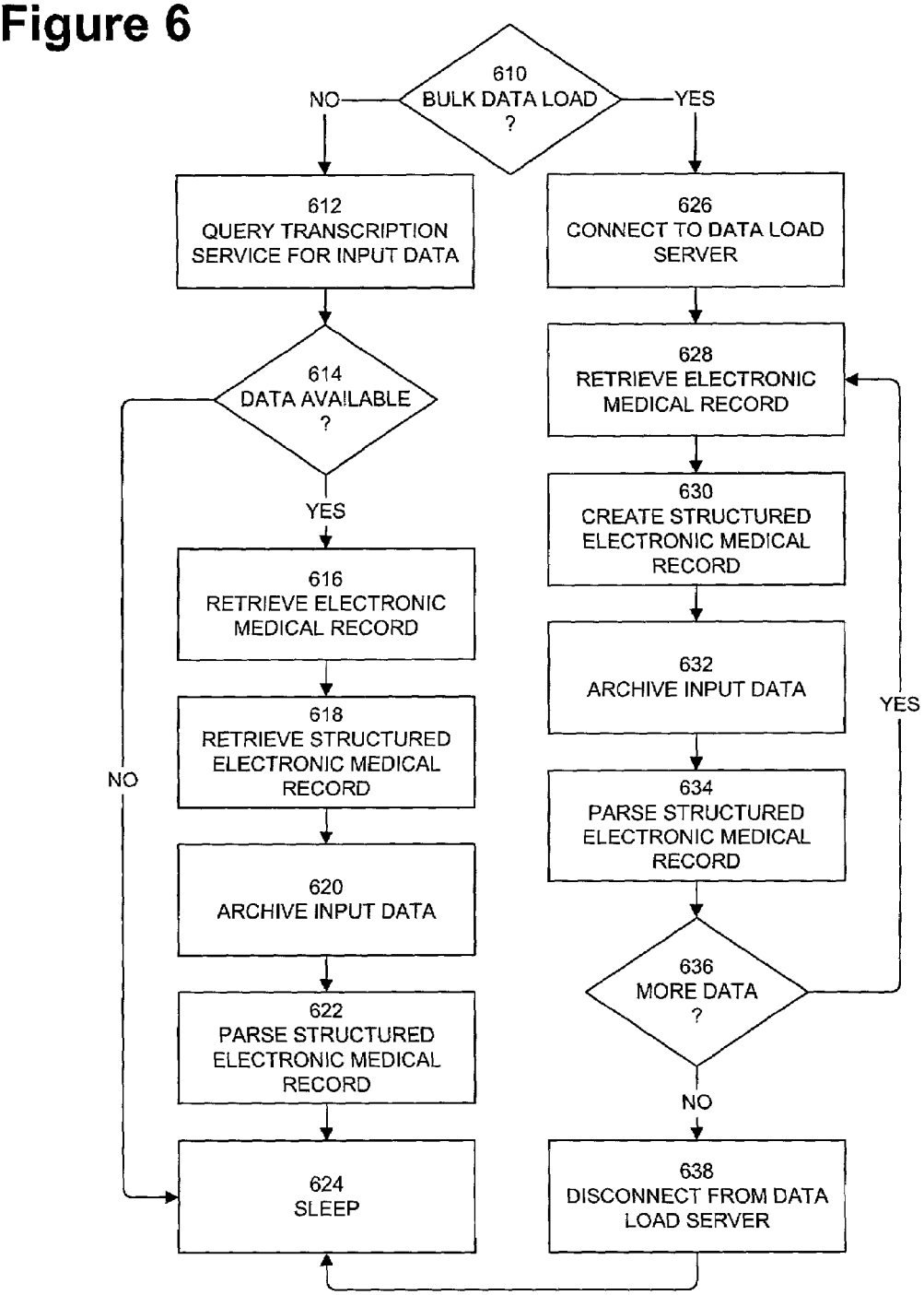
FIG. 6 is a flow diagram of an embodiment of batch download module 310 shown in FIG. 3.

FIG. 6 is a flow diagram of an embodiment of batch download module 310 shown in FIG. 3. The process begins at step 610 by determining whether batch download module 310 is performing a bulk data load. If the answer at step 610 is no, batch download module 310 is performing a periodic retrieval of input data and the process proceeds to step 612. If the answer is "yes", batch download module 310 is performing a bulk download of input data and the process proceeds to step 626.

Figure 7:
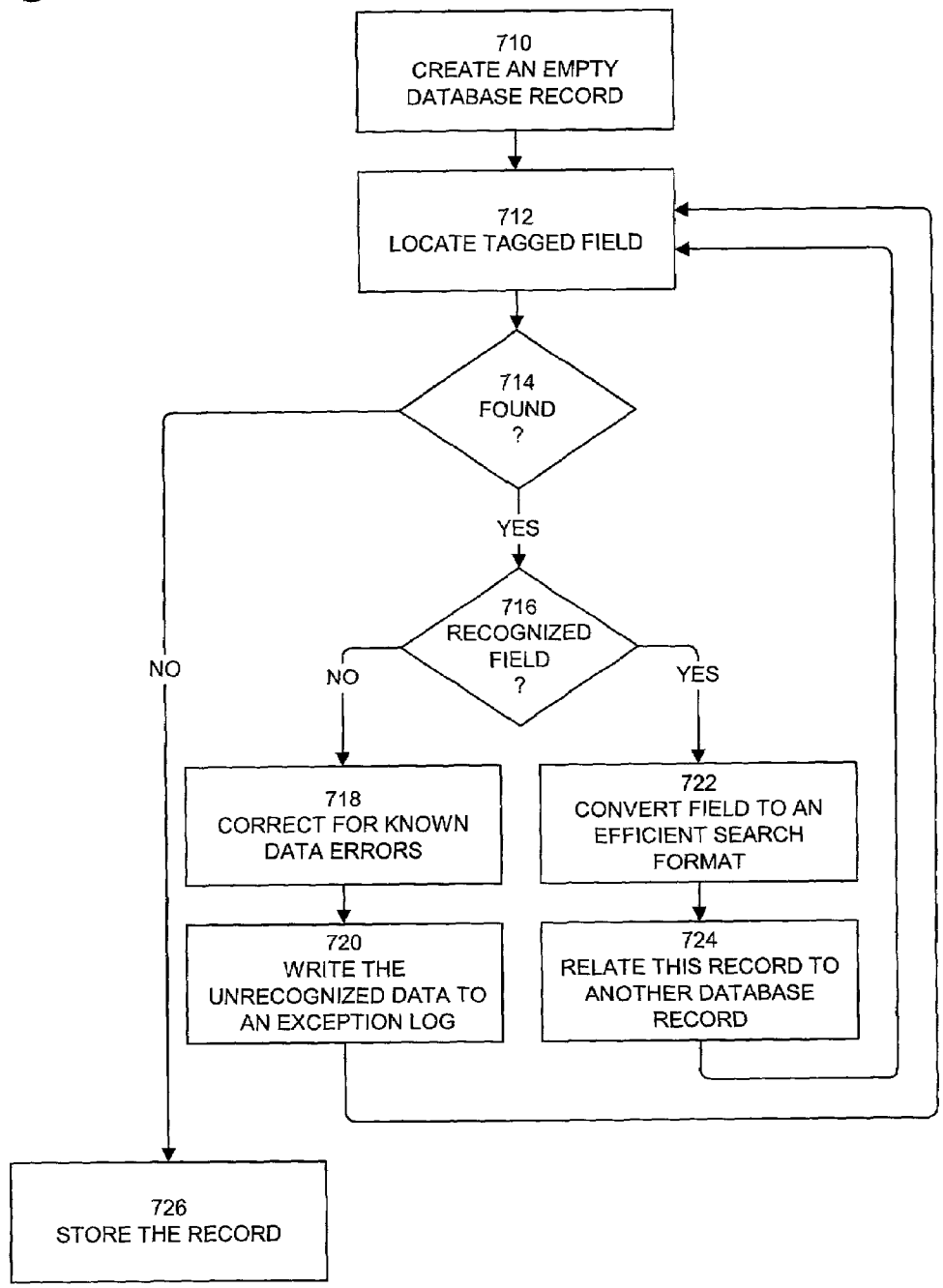
FIG. 7 is a flow diagram of an embodiment of parser module 330 shown in FIG. 3.

Referring to FIGS. 2, 3, and 6, the periodic retrieval of input data begins at step 612 with batch download module 310 issuing a query for input data to transcription service 230. If batch download module 310 determines, at step 614, that no data is available, the process proceeds to step 624 and sleeps until the next retrieval period. If data is available at transcription service 230, the process proceeds to step 616 by retrieving electronic medical record 135 followed by retrieving structured electronic medical record 235 at step 618. At step 620, batch download module 310 stores electronic medical record 135 and structured electronic medical record 235 in archive data 325. At step 622, batch download module 310 parses structured electronic medical record 235. FIG. 7 describes the parsing process in greater detail. Following step 622, the process proceeds to step 624 and sleeps until the next retrieval period.

Referring again to FIGS. 2, 3, and 6, the bulk download of input data begins at step 626 with batch download module 310 connecting to a data load server. The data load server is a general-purpose computer that has direct access to the bulk data. In one embodiment, a network connection facilitates communication between the data load server and data warehouse 260. In another embodiment, the data load server and data warehouse 260 are integrated into a single general-purpose computer platform. At step 628, batch download module 310 begins an iterative process for loading the data by retrieving an electronic record such as electronic medical record 135. At step 630, batch download module 310 converts the electronic record into a structured electronic record such as structured electronic medical record 235. The conversion is similar to the conversion that transcription service 230 performs to create structured electronic medical record 235. At step 632, batch download module 310 stores the electronic record and the structured electronic record in archive data 325. At step 634, batch download module 310 parses the structured electronic record. FIG. 7 describes the parsing process in greater detail. If batch download module 310 determines, at step 636, that more bulk data is available, the process repeats from step 628. If all of the bulk data has been loaded, at step 638, batch download module 310 disconnects from the data load server. Following step 638, the process proceeds to step 624 and sleeps until the next retrieval period.

FIG. 7 is a flow diagram of an embodiment of parser module 330 shown in FIG. 3. The process begins at step 710 by creating an empty database record. At step 712, parser module 330 begins the iterative process of locating a tagged field in structured electronic medical record 235 shown in FIG. 2. Parser module 330 locates the tagged fields in structured electronic medical record 235 and does not process each word to define the meaning of a phrase in the document in the context of a specific domain or canonical grammar. If parser module 330 determines, at step 714, that structured electronic medical record 235 does not contain any more tagged fields, the process stores the record in clinical, diagnostic, and treatment data 332 at step 724. If parser module 330 locates a tagged field, but determines, at step 716, that the tagged field is not recognized, the process attempts to correct for known data errors at step 718. If the error is not a known data error, at step 720, the process writes the unrecognized data to an exception log. A system operator will periodically analyze the exception log and attempt to correct and reprocess the erroneous data. If the tagged field is recognized at step 716, the process converts the field data, at step 722, to a format that will improve the efficiency of a database search using the field. For example, if the field describes the date for the patient visit, the field data in structured electronic medical record 235 consists of "Mar. 28, 2001" stored as a text field of length 10 characters. Since it is not efficient for a database to search text data, step 722 will convert the field data to a "date and time" datatype. The Oracle™ DATE datatype is an exemplary "date and time" datatype and is efficient because it only uses 7 bytes to store the day, month, century, year, hour, minute, and second. After converting the field data, at step 724, the process links this record to another record if the field data uniquely identifies another record in the database. Following step 720 and step 724, the process repeats from step 712.

Figure 8:
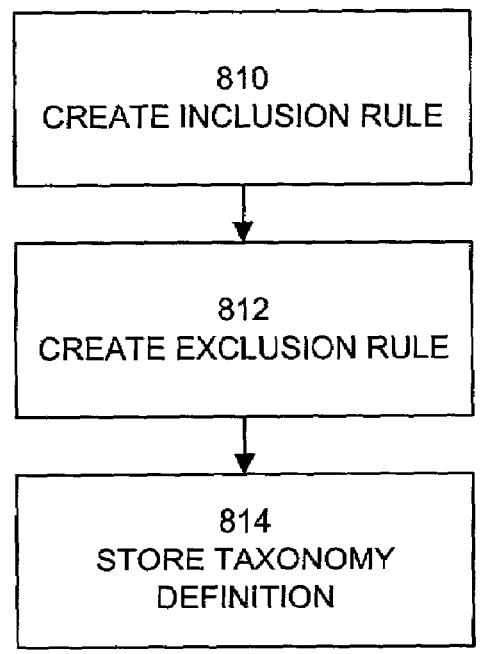
FIG. 8 is a flow diagram of an embodiment of taxonomy definition module 342 shown in FIG. 3.

FIG. 8 is a flow diagram of an embodiment of taxonomy definition module 342 shown in FIG. 3. A taxonomy defines a grouping of the clinical, diagnostic, and treatment data 332 that a database query will return. The characteristics that comprise a taxonomy include a description of an illness, drug prescriptions, medical coverage and treatment plan, family history data, demographic data such as geographic location, gender, and age, the physician's specialty, and clinical diagnostic terms such as myocardial infarction, LDL, heart attack, or bundle branch block. The taxonomy definition process begins at step 810 with the creation of inclusion rules. The inclusion rules define characteristics that must appear in each record comprising the result set generated by running a taxonomy definition. After step 810, the taxonomy definition process creates the exclusion rules at step 812. The exclusion rules define characteristics that must not appear in each record comprising the result set of the database query. After a user creates the inclusion and exclusion rules that comprise the taxonomy definition, the taxonomy definition process stores the taxonomy definition in clinical, diagnostic, and treatment data 332 at step 814.

Figure 9:
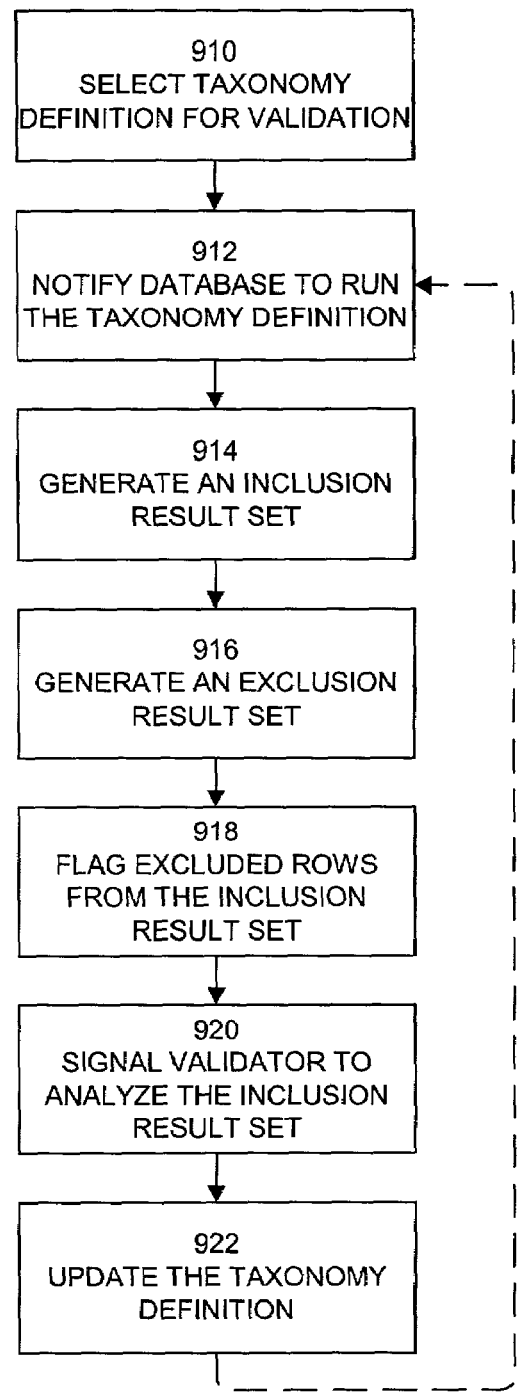
FIG. 9 is a flow diagram of an embodiment of taxonomy validation module 344 shown in FIG. 3.

FIG. 9 is a flow diagram of an embodiment of taxonomy validation module 344 shown in FIG. 3. The taxonomy validation process begins at step 910 when a validator selects a taxonomy definition stored in the database for validation. The selection of the taxonomy definition notifies the database to run the taxonomy definition at step 912. At step 914, the database runs the inclusion rules of the taxonomy definition to generate an inclusion result set. At step 916, the database runs the exclusion rules of the taxonomy definition to generate an exclusion result set. At step 918, the database rows that appear in both the inclusion result set and the exclusion result set are flagged in the inclusion result set. At step 920, the database signals the validator that the inclusion result set is ready for analysis. The analysis involves a row-by-row inspection of the result set. If a row is incorrectly excluded, the validator can remove the exclusion flag for the row and update the taxonomy definition to eliminate the row from the exclusion result set. Similarly, the validator can update the taxonomy definition to include additional rows in the inclusion result set. When the analysis is complete, the validator saves the updated taxonomy definition in the database at step 922 and optionally repeats the process from step 912.

Referring back to FIG. 3, the query builder module 346 allows a user such as a clinical researcher, treating physician or a consulting physician to pose a clinical question and receive a result set that answers the clinical question. Query builder module 346 combines the result set of multiple taxonomy definitions into a single result set.

The present invention relates to a database system containing information useful for clinical, diagnostic, clinical trial recruitment, medical marketing, and other purposes. The database system of the invention has two major advantages over traditional medical database systems:

First, the system comprises a novel data entry method in which relevant clinical information is extracted from virtually any data source including the physician's dictated notes, laboratory reports, EKG, EEG, or other instrument reports, CAT scan, X-ray, functional or imaging studies, or any test that generates a result in an electronic-based medium to create an electronic medical record containing an individual's information, after which the database system tags the data for search and correlative functions. This method is particularly advantageous, not only because it facilitates entry of a large amount of relevant clinical information, but also because it does not require clinicians to change the way they routinely collect such information, for example, by restricting them to questionnaire formats or other fixed data entry means.

Second, the system enables a clinician to obtain valuable, up-to-date information and suggestions for diagnostic testing, and in particular, genetic screening, based upon the patient's clinical information and attributes, without needing to first obtain specific genotype information. The database system of the invention correlates the patients' clinical information including phenotype, specific attributes, and demographic information with information in the data warehouse, and generates suggestions for appropriate genetic, proteonomic, or other diagnostic tests based upon the patients phenotypic attributes. The invention further relates to entering the results of the genetic testing into the system, after which the system generates suggestions for treatment and/or alternative therapy based upon those results.

In one embodiment, the database system contains a plurality of electronic medical records, each record containing clinical information extracted from any relevant clinical source for an individual patient. The electronic medical records of the invention are a particularly important element of the invention because they provide a comprehensive and complete patient record that can be segmented and searched based on virtually any criteria in a broad range of applications. Relevant clinical information contained in the electronic medical records of the invention includes, but is not limited to, phenotype, medical, family, biochemical, physiologic, proteonomic, geographic, diet, exercise, demographic, drug reaction history, drug prescriptions, laboratory results, and past diagnoses and treatments. By way of example, the database can optionally contain information selected from the group comprising medication being taken by the individual, medical history, occupational information, information relating to the hobbies of the individual, diet information, family history, normal exercise routines of the individual, age, and sex. More specific examples of information include whether the individual is undergoing hormone replacement therapy, whether the individual is a drinker or a smoker, whether the patient regularly uses a sun-tanning bed, the geographic region in which the patient resides, and whether the patient is pre- or post-menopausal. In one embodiment, the phenotype and chemical information is collected at the same time from the individual, so that the information is of the most relevance to the phenotype.

In another embodiment, the invention relates to a database system wherein the electronic medical record includes the patient's genotype and/or haplotype information. By way of example, genotype and haplotype information includes, but is not limited to, information relating to chromosome structure, DNA or RNA sequence, length of a specific gene or region, gene expression, such as mRNA or transcription levels, identification of one or more single nucleotide polymorphisms (SNPs), and/or any other information relating to a patients genetic makeup. Alternatively, or additionally, the genotype information can comprise a record of actual or inferred DNA base sequences at one or more regions within the genome. Still further, the genotype information can comprise a record of variation between a specified sequence on a chromosome of that individual compared to a reference sequence, indicating whether, and to what extent, there is a variation at identical positions within the sequence. The genotype information can also comprise a record of the length of a particular sequence, or a particular sequence variant, such information being of use to investigate absence or presence of correlation between genetic variation and phenotype variation.

In many applications of this invention, it is contemplated that an individual's genotype information, such as, for example, SNP information, will be unknown at the time when they are examined by their physician. Therefore, according to the invention, the physician would enter the patient's clinical data including medical history, attributes, demographic, or laboratory test results into the database. The system would then correlate the patient's clinical information with information in the database, and/or accessed from one or more public or private domain databases, and generate a suggestion for a specific genetic test. In addition, the patient's clinical information may be compared with other patient records in the database to determine whether common attributes are present in the population identified by the system of the invention as sharing a common SNP. Information would then be communicated to the physician indicating that the individual shares attributes with a population of individuals having a common SNP. Accordingly, this method also provides a means for identifying patients which would be good candidates for clinical trials.

In another embodiment, the present invention relates to a method for determining a patient's disease risk and susceptibility type. Disease prevention will assume increasing importance in future healthcare strategies in areas such as congestive heart failure, cancer, neurological, and other degenerative diseases. The method comprises extracting clinical information from any source to create a patient record in the form of an electronic medical record, correlating the patient's clinical information with information in the system and/or accessed from one or more public or private domain databases, such as the SNP Consortium, and generating a result set that includes a suggestion for genetic, proteonomic, and/or other type of diagnostic testing.

In a further embodiment, the present invention also relates to displaying the identified correlation to aid in determining the statistical significance of the identified correlation.

In another embodiment, the present invention further relates to inputting the results of the genetic, proteonomic, and/or other diagnostic test into the system, and generating a result set that includes a suggestion for treatment based upon the test result and the patient's record.

In another embodiment, the present invention relates to a method for identifying a patient with a drug response polymorphism comprising creating a patient record by entering the patient's clinical information including drug response information, correlating the patients information with information in the system and/or accessed from one or more public or private domain databases relating to single polynucleotide polymorphisms (SNPs), and generating a result set that includes a suggestion for genetic testing of possible SNPs identified to be correlated with the drug response.

In a further embodiment, the present invention further relates to the step where the result of the genetic test is entered, and the system generates a suggestion for an alternative drug therapy based upon the patient's record.

Many SNPs have been identified, although their significance is still unknown. Drug metabolizing enzymes, and their SNPs have been identified, and patients can be tested inexpensively on, for example, a rapid sequence analyzer, PCR, restriction fragment length polymorphism, micro-chip array technology, or any other methods well known in the art. The missing link, however, is the access to clinical information to identify patients in whom genetic testing is warranted. The present invention provides this link by enabling a clinician to correlate phenotypic information with specific genotype information. This clinical information is vital to offer appropriate genetic testing when indicated by demographic and clinical information in the patient record.

In another embodiment, the present invention also relates to a method for identifying a subject for a clinical trial comprising extracting clinical information to create a patient record in the form of an electronic medical record, correlating the patient's clinical information with other patient records in the system, identifying a population, or sub-population of patients having similar phenotypes, genotypes, or clinical characteristics, and identifying clinical trials which would be appropriate for the patient's participation.

Approximately 65% of clinical trials do not finish on time primarily due to delays in recruitment of patients. The average clinical trial delay due to recruitment is in excess of three months and costs trial sponsors $1.3 million per day. Part of the problem is that sponsors rely almost 100% of the time on the treating physician or his research staff to screen and enroll patients in clinical trials. Efforts to use the internet, radio/TV and other media to "recruit" clinical trial candidates have been minimally successful, especially when the targeted patient population has a chronic disease accompanied by a sometimes complicated treatment regimen. More often than not patients trust their personal physician to advise them on all their treatment options.

Under current practice, the sponsor of the clinical trial awards a clinical trial to a physician, or physician group, that have participated in clinical trials in the past, and as importantly have large numbers of patients in their practice from which to potentially draw from. The problem arises from the fact that an overwhelming majority of these practices do not have the ability to search any kind of database to perform a suitability check, or as it is known in the industry, "screening" for patients based on detailed, multi-dimensional, "inclusion/exclusion" criteria—meaning patients on multiple drug therapies may or may not allow the patient to be included, past medical history may or may not exclude the patient, etc. Because their medical records a paper-based, to search them manually would be close to impossible and cost prohibitive. As a result, physicians or their research staff generally wait until a patient is seen in the office, and only then, if they remember, do they initiate the screening and recruitment process. This process is not only extremely inefficient, but also will cost sponsors hundreds of millions of dollars in lost sales revenues.

The present invention provides a system that solves the problem by utilizing the data warehouse and search functions to screen a large pool of patients automatically and with greater accuracy using the inclusion/exclusion and validation functions described herein. For example, a particular patient might be a qualified candidate for a clinical trial, except for the fact that he has Type II, insulin-dependent diabetes and takes a cholesterol lowering drug. According to the invention, the system enables the user to include or exclude subjects based on detailed information and perform faster clinical trial screening and enrollment with less administrative and resource costs on the part of the physicians and the research industry.

This invention further provides a system for identifying sub-populations and/or individuals that share common phenotypic or genetic characteristics. The identification of such sub-populations or individuals provide useful information for research, diagnostic or therapeutic purposes. For example, according to one embodiment of the invention, a sub-population of individuals is identified having common phenotypic characteristics based upon shared attributes identified in the database. Individuals in the sub-population may then be further evaluated to determine if they share, for example, a common genotype, a previously unidentified characteristic, or an idiosyncratic response to drug treatment. The identification of such sub-populations is particularly useful for identifying test and appropriately matched control populations in connection with the clinical evaluation of drug therapies.

In a further embodiment, the identification of individuals from the database, according to the invention, also enables physicians to identify those individuals likely to have a specific disease or disorder based upon common attributes. Such identified individuals may therefore be candidates for further diagnostic testing, e.g., genetic testing or screening for specific mutations.

In yet another embodiment, information relevant to making specific treatment decisions for individuals may be provided, according to this invention, by identifying common attributes among a sub-population of individuals in the database and communicating relevant information to a physician concerning a patient having attributes in common with others in the sub-population.

In yet a further embodiment, the system can be used to perform market research. Frequently, companies must make sophisticated development and marketing decisions by purchasing and utilizing sub-optimal information that provides a poor clinical representation of targeted patient populations in the market place.

For example, prescription information acquired from a pharmacy only represents a cohort of prescriptions that have been "filled" on a physician and brand-specific basis, e.g. the pharmacy filled four brand-name cholesterol-lowering drug prescriptions, two generic brand cholesterol-lowering drug prescriptions, and one brand-name arthritis medication prescription that a specific physician wrote for his five patients. First, this data set does not track "written versus filled" leaving a void in the efforts to monitor patient compliance. Second, there are no longitudinal support data regarding age, sex, past medical history, diagnosis, and/or other relevant conditions or problems. The data only represents only what is identifiable through prescriptions "filled" and does not accurately represent physicians' overall "treatable" patient populations. Utilizing information garnered from insurance claims data presents the same problem for companies attempting to gain insight into physician and patient populations where the need for clinical and demographic specificity exists.

The present invention provides a system and method which aggregates and imports archived and prospective digitized patient information from the network into a data warehouse. Once in the data warehouse, the system segments and searches patient populations based upon characteristics such as age, sex, diagnosis, co-morbid conditions, past medical history, family history, past surgeries or procedures, diagnostic testing results, lab values, past and current medications and referring physician.

The present invention has many advantages. First, users are able to focus their inquiries and efforts on targeted patient populations based on validated, rich clinical criteria contained in the electronic medical records of the invention. For example, according to the invention, an electronic medical record may contain the following information: a 54 year-old, sedentary, Hispanic female, former smoker, with a stable angina and a family history of diabetes and heart disease, is a Type II insulin dependent diabetic, who has had a cardiac catheter but no subsequent interventional procedures, is taking drug "X" for hypertension, drug "Y" for her cholesterol, and whose LDL levels have been greater than 175 for one year or more. Being able to access all, or part of this type of the de-identified data (i.e., data that has been cleansed to remove personal information such as name, address, and social security number) has been deemed a critical part for mapping a clinical research strategy, or planning for the marketing launch of a new therapeutic approach.

In addition, having the ability to access more robust clinical information gives users and companies the ability to direct their energies toward targeted patient cohorts that will yield not only a historical perspective of the patients past clinical profile, but more importantly, will set up scenarios whereby treatment plans and products can be targeted and tracked to validate clinical and marketing claims. Moreover, companies can focus their marketing efforts and messages to the clinical community based on a more representative data set. In yet another embodiment, the de-identified, aggregate patient data of the invention can be used to create and test "virtual" clinical trial protocol development for clinical trial planning using rich, segmented population-based information.

In yet a further embodiment, the present invention can be used to perform marketing services, where it is imperative that marketers identify the targeted population and the conventional therapy they are seeking to replace. Field marketing teams are not trained or enabled to drive effective patient recruitment in physicians offices for Phase IV studies. Although pharmaceutical companies encourage physicians to accept on face value the results of their clinical trials, they always attempt to enhance the marketing of their newly approved drug by focusing on Phase IV market-centered studies.

However, since the data that companies purchase generally do not accurately reflect market conditions, e.g. the data covers the "number" of name-brand prescriptions a physician may have written, but not for "whom" they were written, the companies do not know (and cannot know) which patients are potential candidates for a new drug. In addition, most physicians practices utilize paper-based charts, and cannot readily identify which patients are prescribed what drugs without doing a manual chart audit. Such a task is daunting, if not impossible to perform given time pressures and declining resources in physicians offices. This is extremely costly and time consuming for companies, and a burden, if not a barrier, for companies to recruit physicians to participate in Phase IV initiatives.

The present invention provides a system and method for importing both historical data and continuing to populate the data warehouse with prospective data, which the system can then segment all patients, for example, "by physician", "location", and "by date seen", and who prescribed a given drug for a given patient with a specific clinical profile. With the consent of the patient and physician, the data could be stored and shared with companies developing alternative therapies, thereby enabling companies to target those patients who would potentially benefit from the proposed switching strategy, hence driving the awareness of the products proposed benefits and market acceptability. In addition, using the same technology, the system is able to generate practice based reports that allow companies or users to track compliance measures and perform compliance audits and improve physician-patient communications.

The present invention relates to the application of the system and methods described herein in a broad variety of disease categories including, but not limited to, cancer, heart disease, diabetes, hypertension, mental illness, allergies, arthritis, infectious, neurological and immunological diseases. Diseases that can be diagnosed or treated according to the present invention include any disease for which the database of this invention identifies a common constellation of specific phenotypic and/or genetic features. In addition, those skilled in the art would recognize that the system and methods described herein can be utilized for virtually any application for which the data would be useful.

Referring again back to FIG. 3, the web distribution module 352, report generation module 354, and download module 356 comprise the output modules for data warehouse 250. Each module generates output by either retrieving data from archive data 325 or obtaining a result set from a query performed by query builder module 346. The data and reports comply with the Health Insurance Portability and Accountability Act (HIPAA) and, since each module determines authorization and authentication at the customer level, the access to the output is restricted based on the login identification of a customer. Web distribution module 352 uses a browser-based graphical user interface to view or print clinical notes, request reports, clinical trial reports, or data warehouse service updates. Report generation module 354 allows the customer to create and save custom report formats. Download module 356 allows a customer to transfer the output data to a local storage device.

Figure 10:
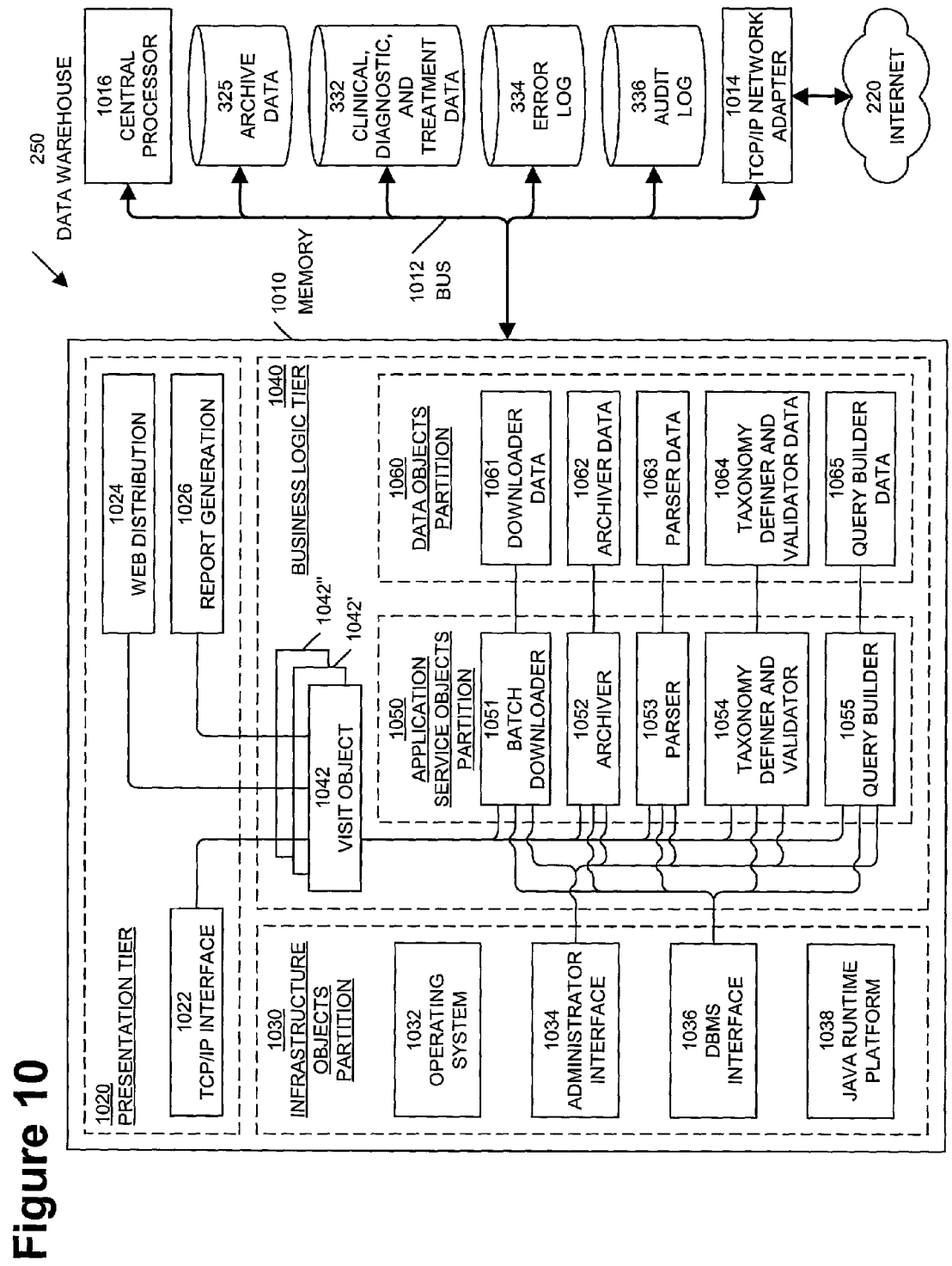
FIG. 10 is a functional block diagram of an embodiment of the system for storing and retrieving clinical, diagnostic, and treatment data illustrating the configuration of the hardware and software components.

FIG. 10 is a functional block diagram showing the hardware and software components that comprise data warehouse 250. Bus 1012 couples central processor 1016, archive data 325, clinical, diagnostic, and treatment data 332, error log 334, audit log 336, and transmission control protocol/internet protocol (TCP/IP) adapter 1014 to memory 1010. TCP/IP adapter 1014 is further coupled to network 220 and is the mechanism that facilitates the passage of network traffic between data warehouse 250 and network 220. Central processor 1016 performs the methods disclosed herein by executing the sequences of operational instructions that comprise each computer program resident in, or operative on, memory 1010.

FIG. 10 shows the functional components of data warehouse 250 arranged as an object model. The object model groups the object-oriented software programs into components that perform the major functions and applications in data warehouse 250. A suitable implementation of the object-oriented software program components of FIG. 10 may use the Enterprise JavaBeans specification. The book by Paul J. Perrone et al., entitled "Building Java Enterprise Systems with J2EE" (Sams Publishing, June 2000) provides a description of a Java enterprise application developed using the Enterprise JavaBeans specification. The book by Matthew Reynolds, entitled "Beginning E-Commerce" (Wrox Press Inc., 2000) provides a description of the use of an object model in the design of a Web server for an Electronic Commerce application.

The object model for memory 1010 of data warehouse 250 employs a three-tier architecture that includes presentation tier 1020, infrastructure objects partition 1030, and business logic tier 1040. The object model further divides business logic tier 1040 into two partitions, application service objects partition 1050 and data objects partition 1060.

Presentation tier 1020 retains the programs that manage the graphical user interface to data warehouse 250 for industry customer 260. In FIG. 10, presentation tier 1020 includes TCP/IP interface 1022, web distribution 1024 and report generation 1026. A suitable implementation of presentation tier 1020 may use Java servlets to interact with industry customer 260 via a network transmission protocol such as the hypertext transfer protocol (HTTP) or secure HTTP (S-HTTP). The Java servlets run within a request/response server that handles request messages from industry customer 260 and returns response messages to industry customer 260. A Java servlet is a Java program that runs within a Web server environment. A Java servlet takes a request as input, parses the data, performs logic operations, and issues a response back to industry customer 260. The Java runtime platform pools the Java servlets to simultaneously service many requests. TCP/IP interface 1022 uses Java servlets to function as a Web server that communicates with industry customer 260 using a network transmission protocol such as HTTP or S-HTTP. TCP/IP interface 1022 accepts HTTP requests from industry customer 260 and passes the information in the request to visit object 1042 in business logic tier 1040. Visit object 1042 passes result information returned from business logic tier 1040 to TCP/IP interface 1022. TCP/IP interface 1022 sends these results back to industry customer 260 in an HTTP response. TCP/IP interface 1022 uses TCP/IP network adapter 1014 to exchange data via network 220.

Infrastructure objects partition 1030 retains the programs that perform administrative and system functions on behalf of business logic tier 1040. Infrastructure objects partition 1030 includes operating system 1032, and an object oriented software program component for system administrator interface 1034, database management system (DBMS) interface 1036, and Java runtime platform 1038.

Business logic tier 1040 retains the programs that perform the substance of the system for storing and retrieving clinical, diagnostic, and treatment data. Business logic tier 1040 in FIG. 10 includes multiple instances of visit object 1042. A separate instance of visit object 1042 exists for each client session initiated by either web distribution 1024 or report generation 1026 via TCP/IP interface 1022. Each visit object 1042 is a stateful session bean that includes a persistent storage area from initiation through termination of the client session, not just during a single interaction or method call. The persistent storage area retains information associated with industry customer 260 from FIG. 2. In addition, the persistent storage area retains data exchanged between data warehouse 250, transcription service 230, physician 110, clinical provider 115, or third party database 215 via TCP/IP interface 1022.

When industry customer 260 accesses a program in application service objects partition 1050, a message is sent to TCP/IP interface 1022 to invoke a method that creates visit object 1042 and stores connection information in visit object 1042 state. Visit object 1042, in turn, invokes a method in the program. Even though FIG. 10 depicts central processor 1016 as controlling each program in application service objects partition 1050, it is to be understood that the function performed each program can be distributed to a separate system configured similarly to data warehouse 250.

The object model divides business logic tier 1040 into an application service objects partition 1050 and a data objects partition 1060. The programs that reside in application service objects partition 1050 comprise batch download 1051, archiver 1052, parser 1053, taxonomy definer and validator 1054, and query builder 1055. The programs that reside in application service objects partition 1050 include C, C++, Java, Java Server Pages, Oracle scripts, and other scripting programs. The objects that comprise data objects partition 1060 include download data 1061, archiver data 1062, parser data 1063, taxonomy definer and validator data 1064, and query builder data 1065. Each program in the application service objects partition 1050 has a counterpart in the data objects partition 1060 that stores input, intermediate, and output data for the program. The processes performed by batch download 1051 and archiver 1052 are shown in FIG. 6 and discussed above. The process performed by parser 1053 is shown in FIG. 7 and discussed above. The process performed by taxonomy definer and validator 1054 is shown in FIG. 8 and FIG. 9 and discussed above. The process performed by query builder 1055 is discussed above.

Figure 11:
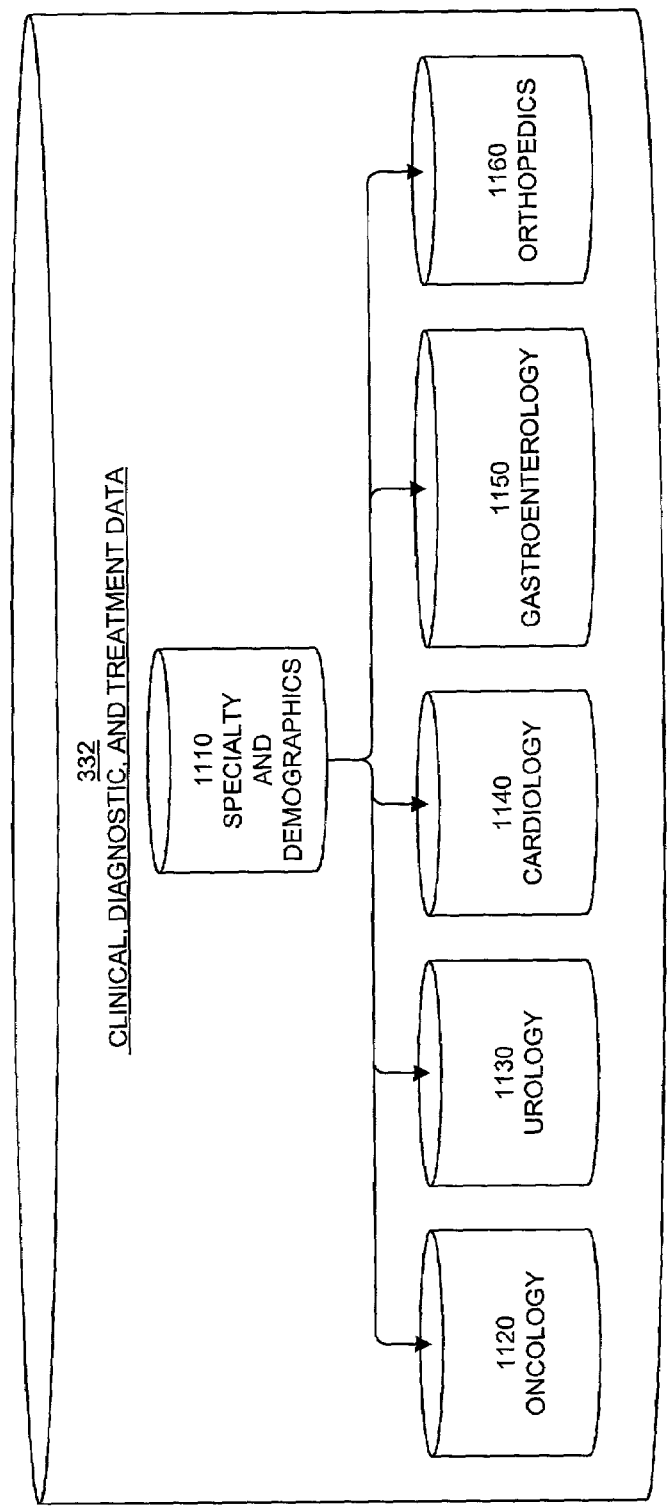
FIG. 11 illustrates a structure of clinical, diagnostic, and treatment data 332 shown in FIG. 3.
Figure 12A:
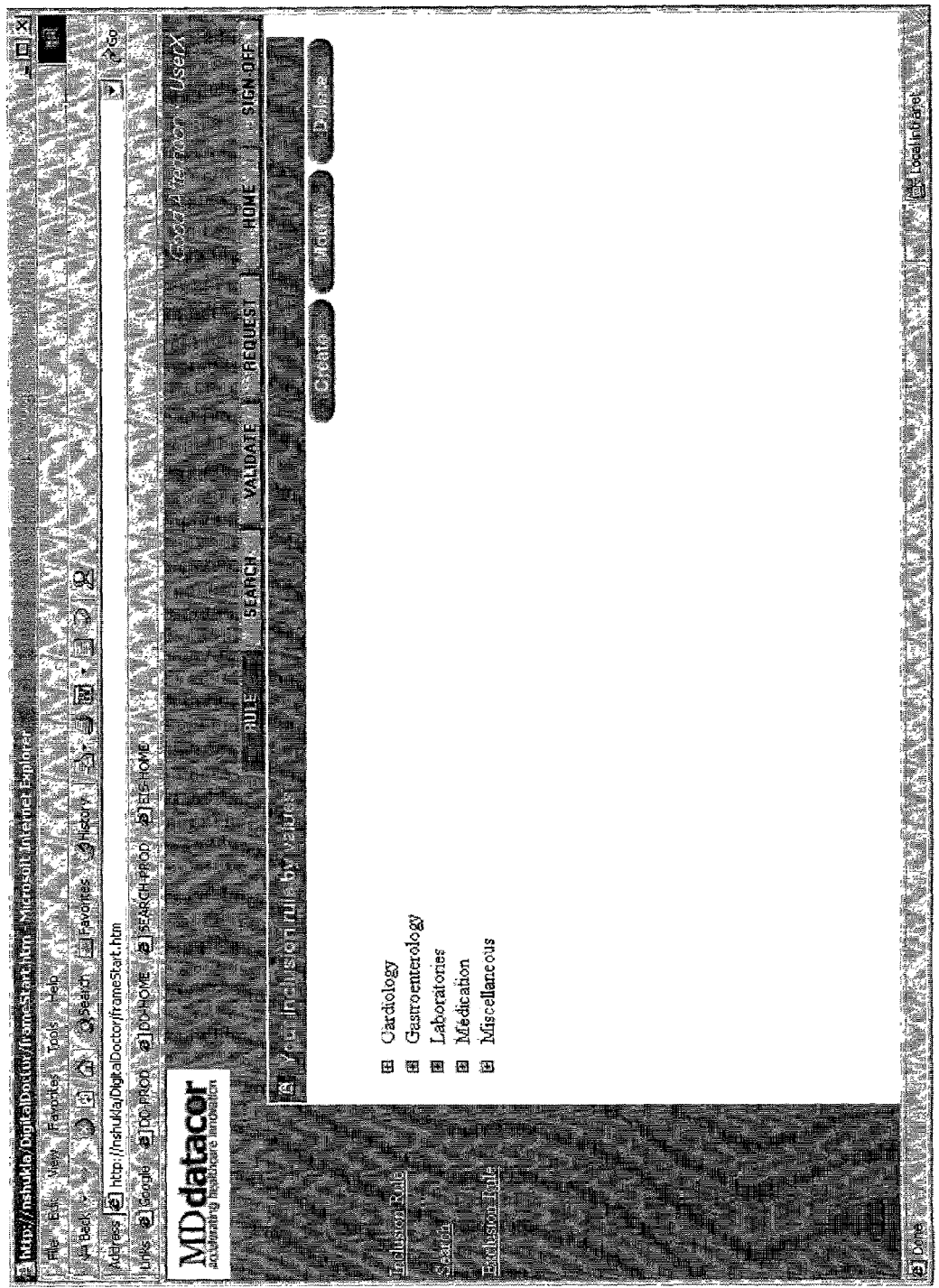
FIGS. 12A through 12F are sample screen snapshots that illustrate the creation of a taxonomy definition that may result from the flow diagram of FIG. 8.
Figure 12B:
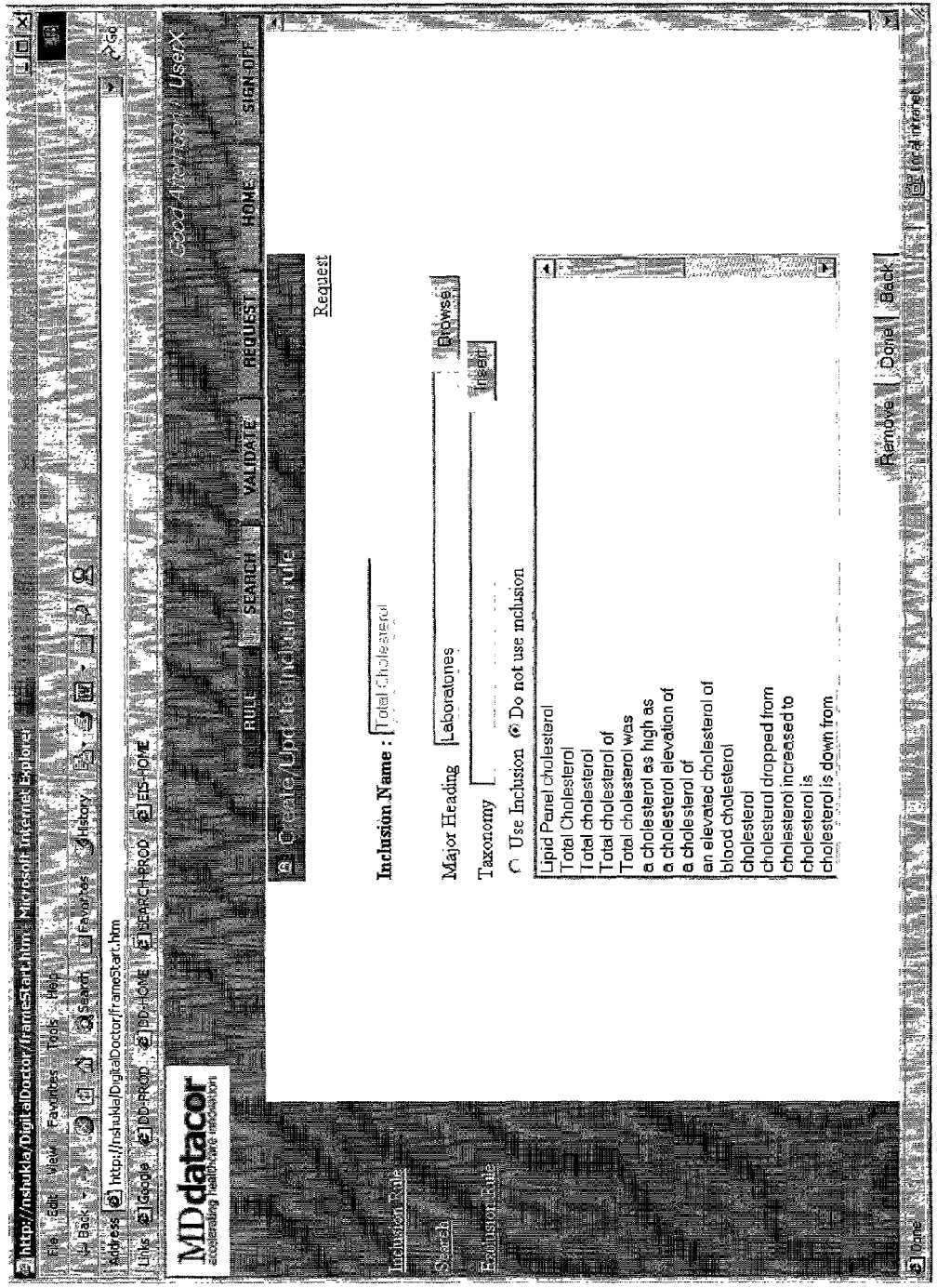
Figure 12C:
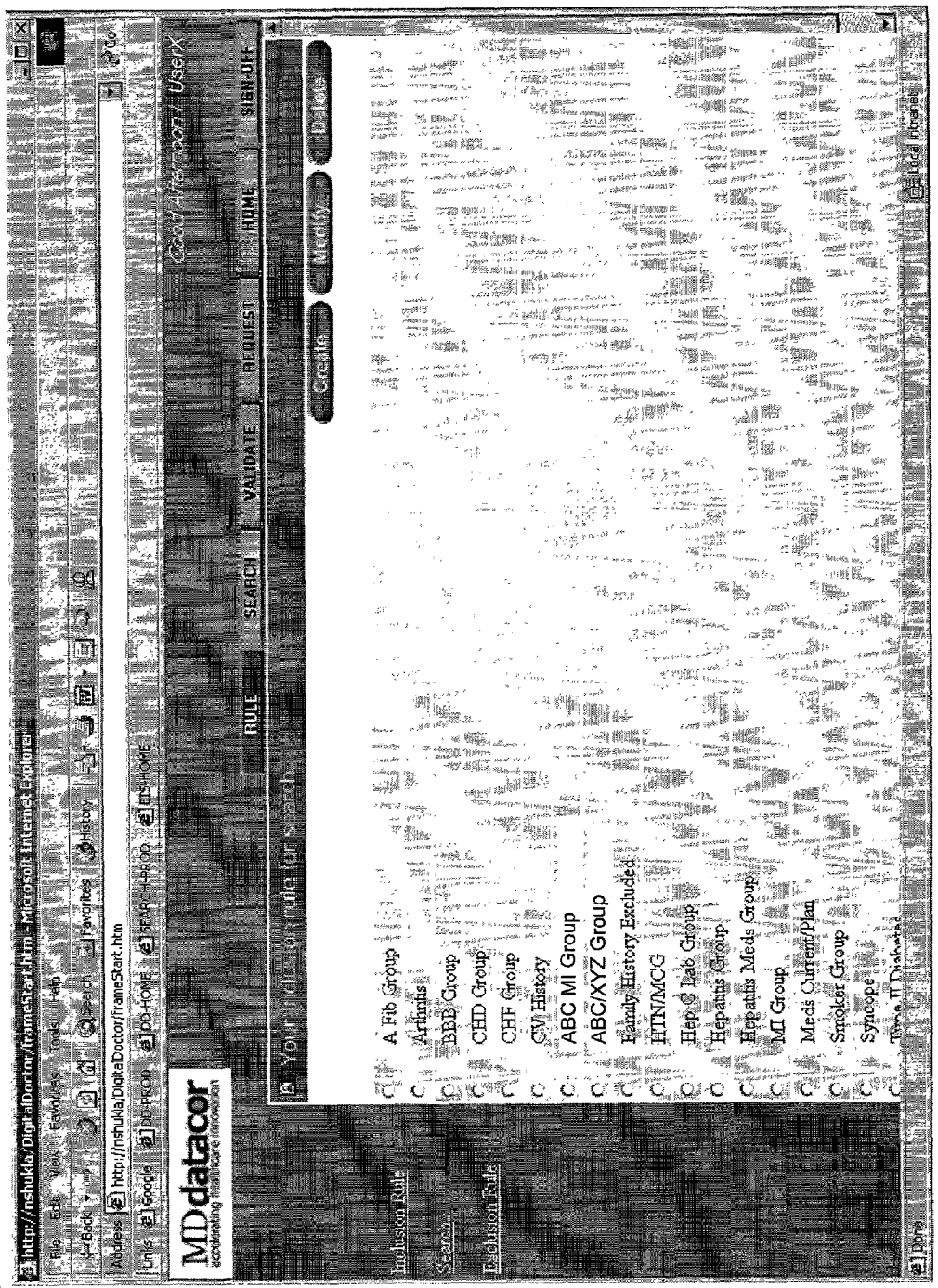
Figure 12D:
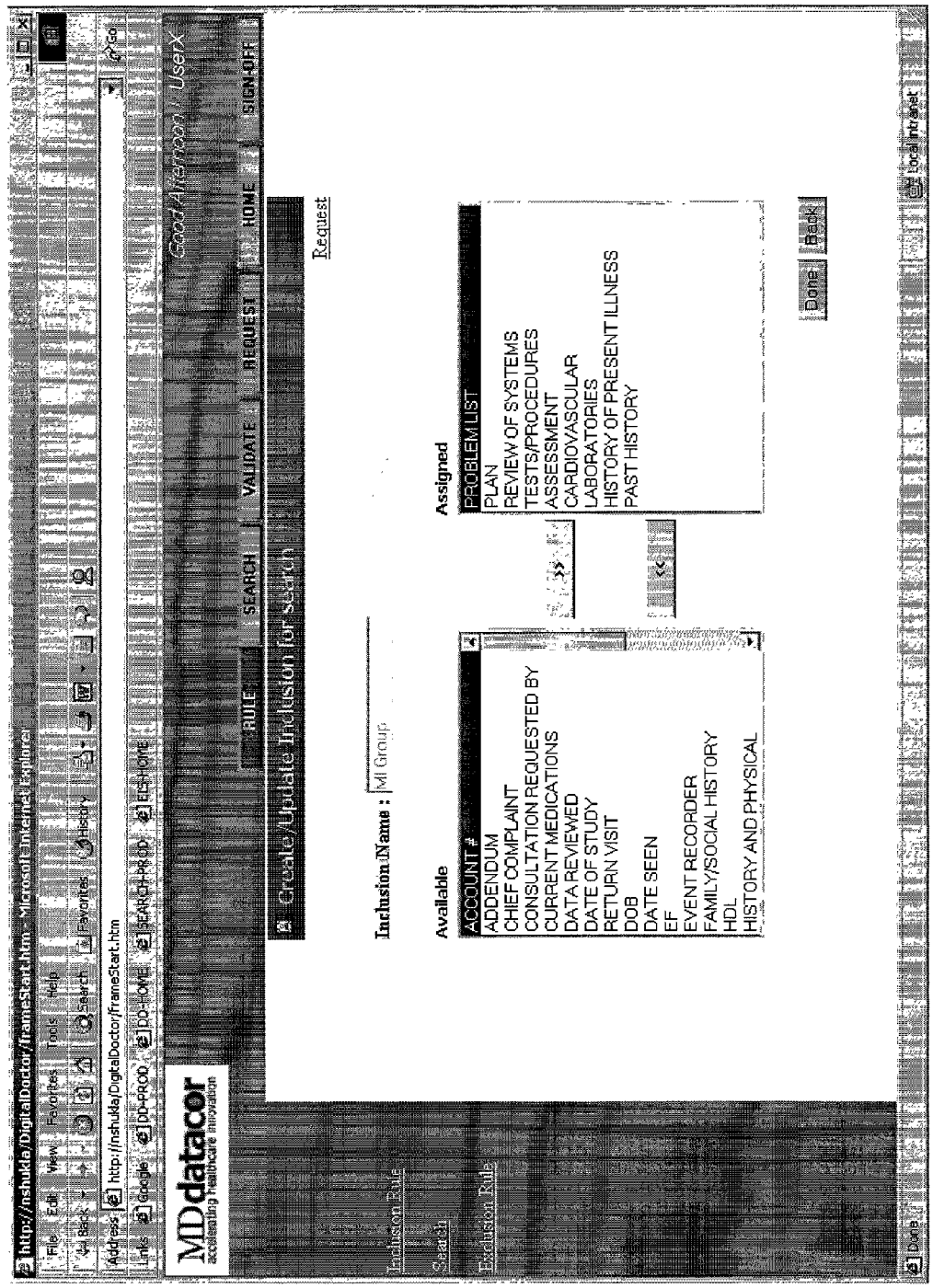
Figure 12E:
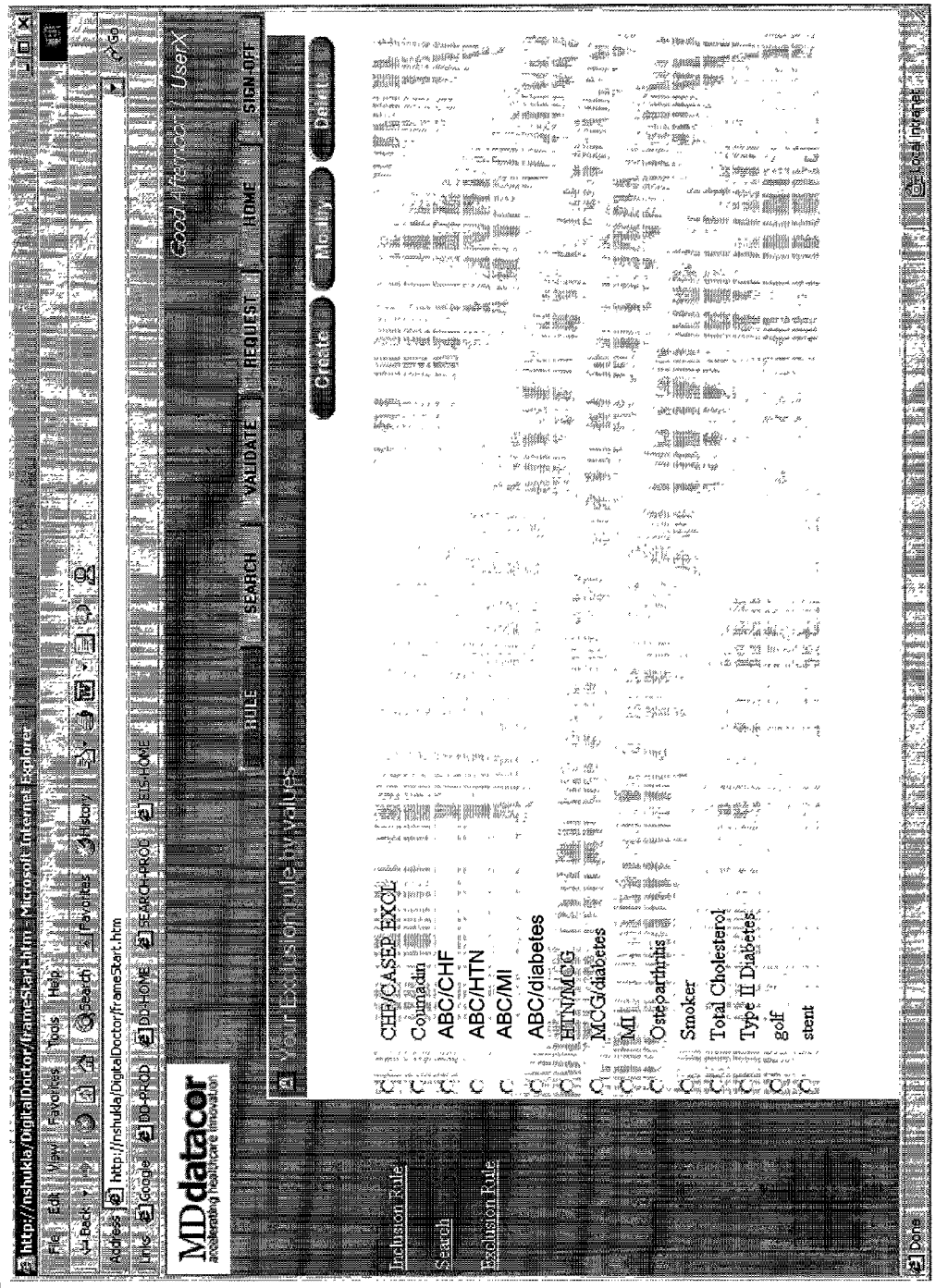
Figure 12F:
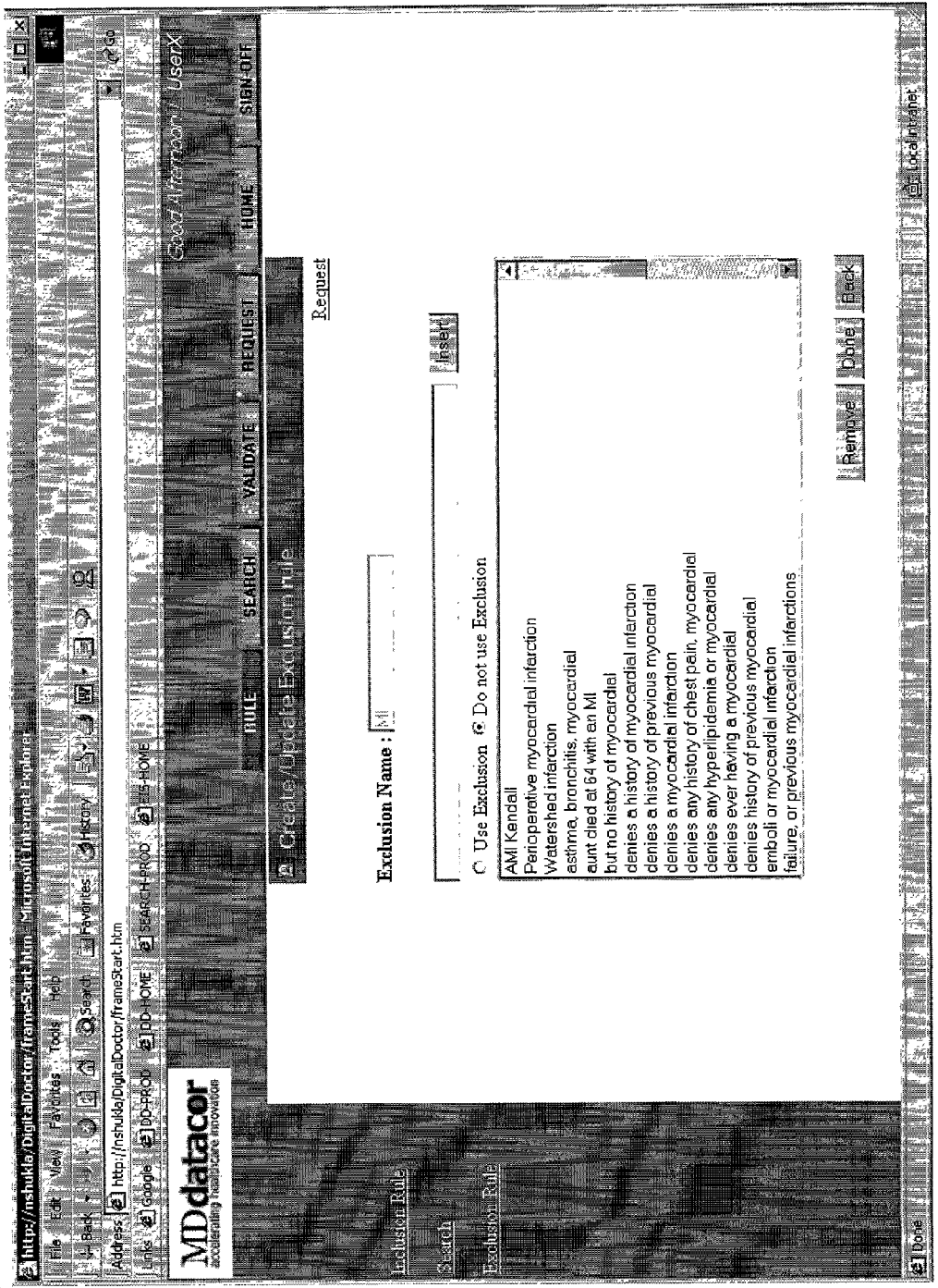
Figure 13A:
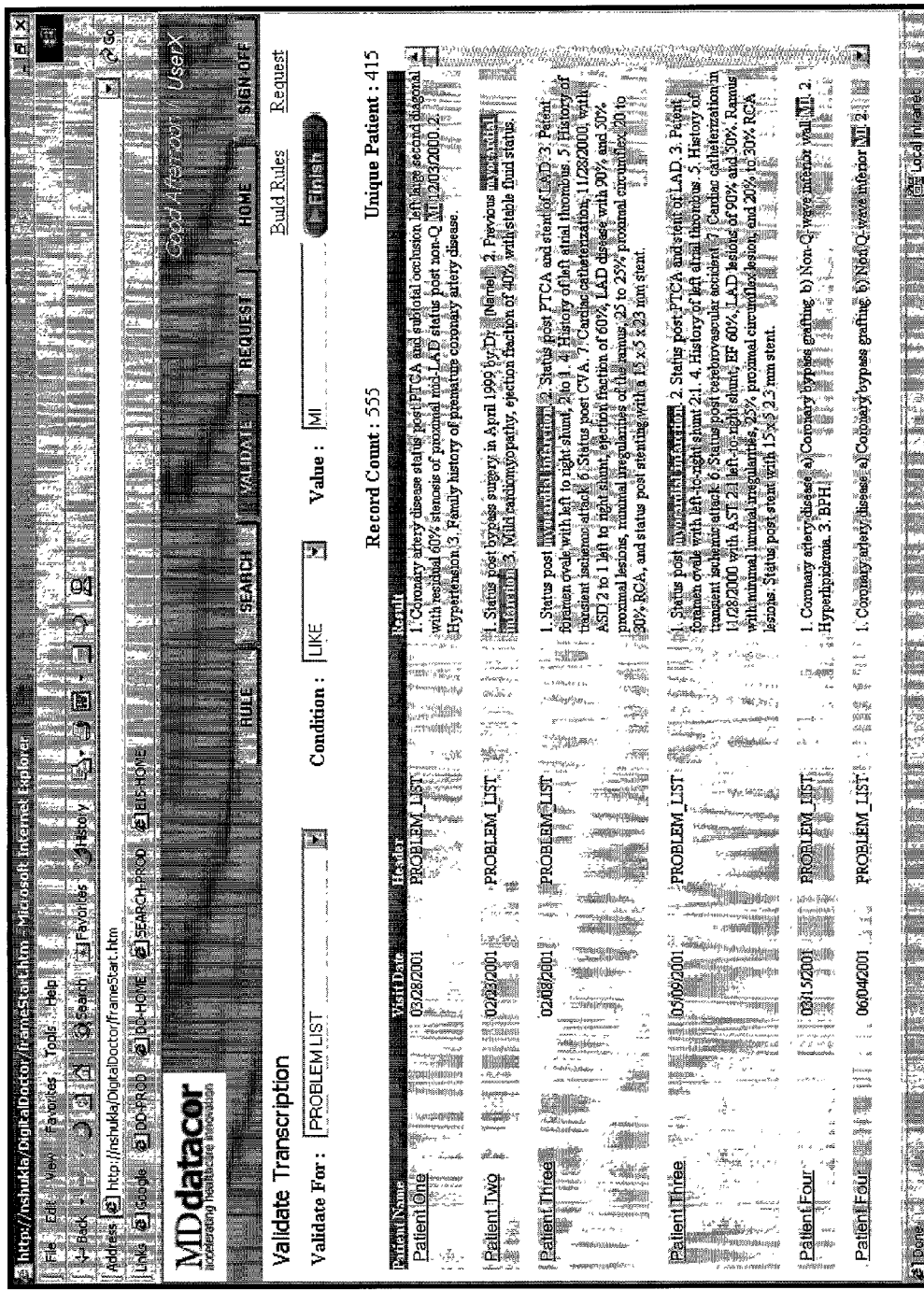
FIGS. 13A through 13B are sample screen snapshots that illustrate the validation of a taxonomy definition that may result from the flow diagram of FIG. 9.
Figure 13B:
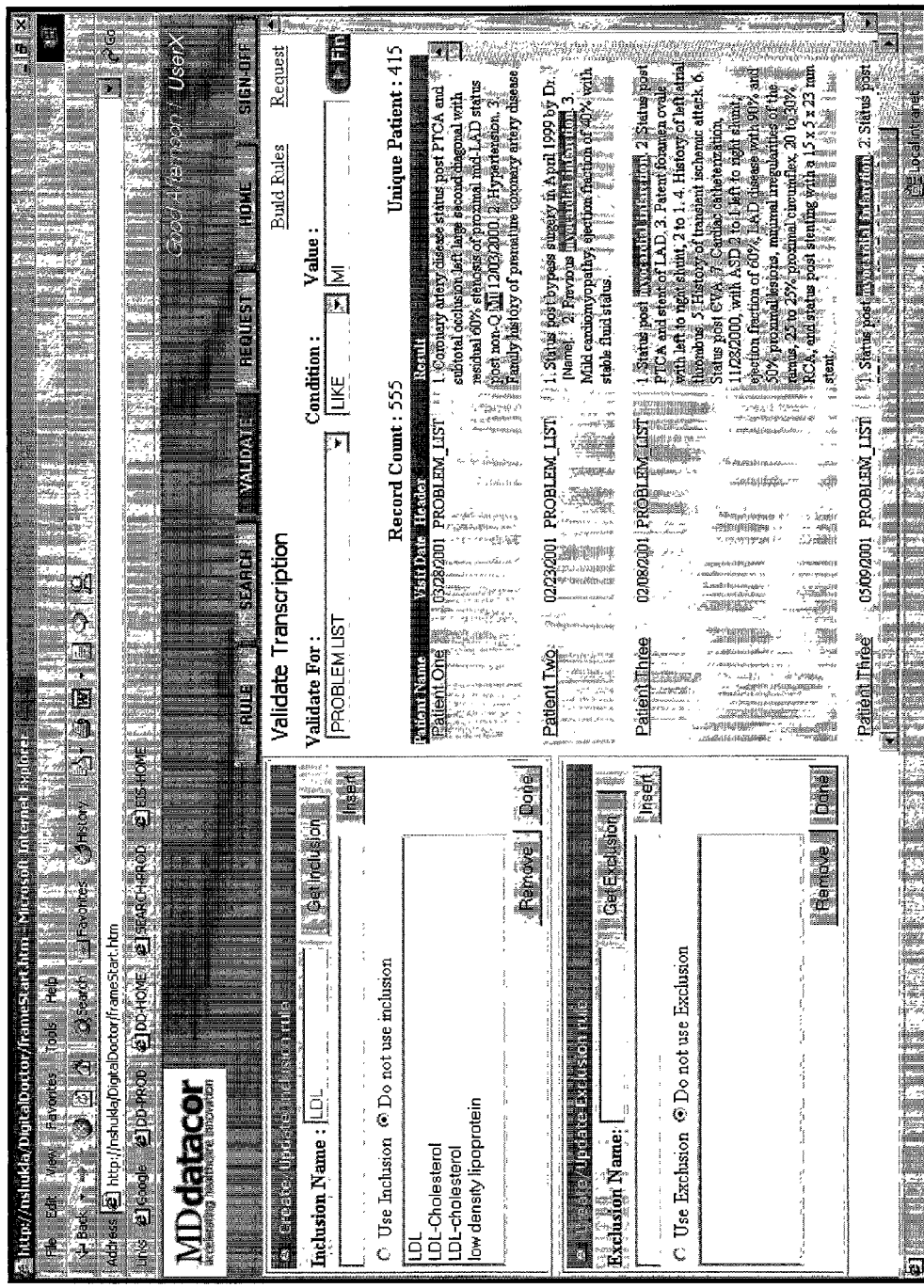
Figure 14A:
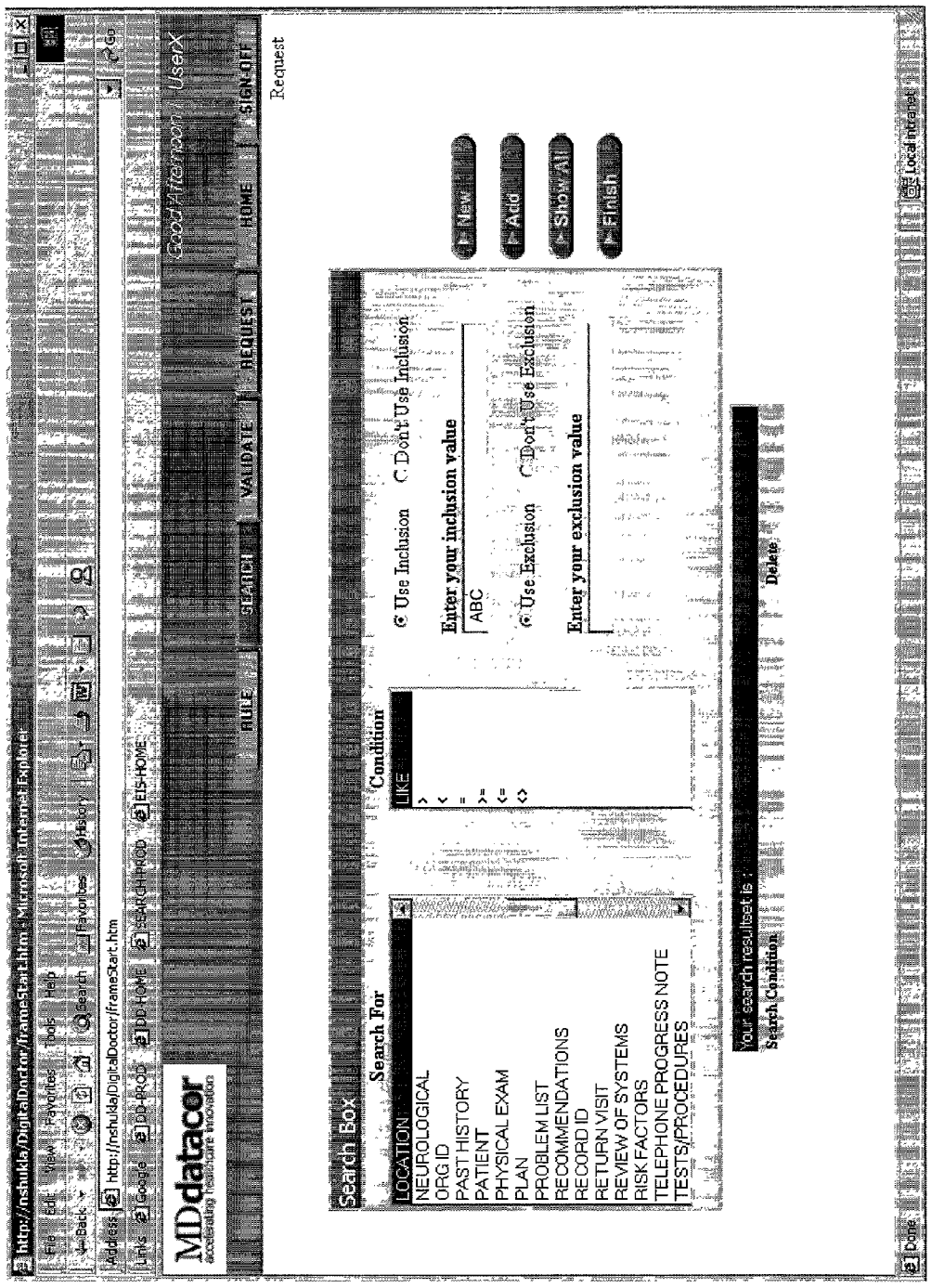
FIGS. 14A through 14E are sample screen snapshots that illustrate a search of the data warehouse.
Figure 14B:
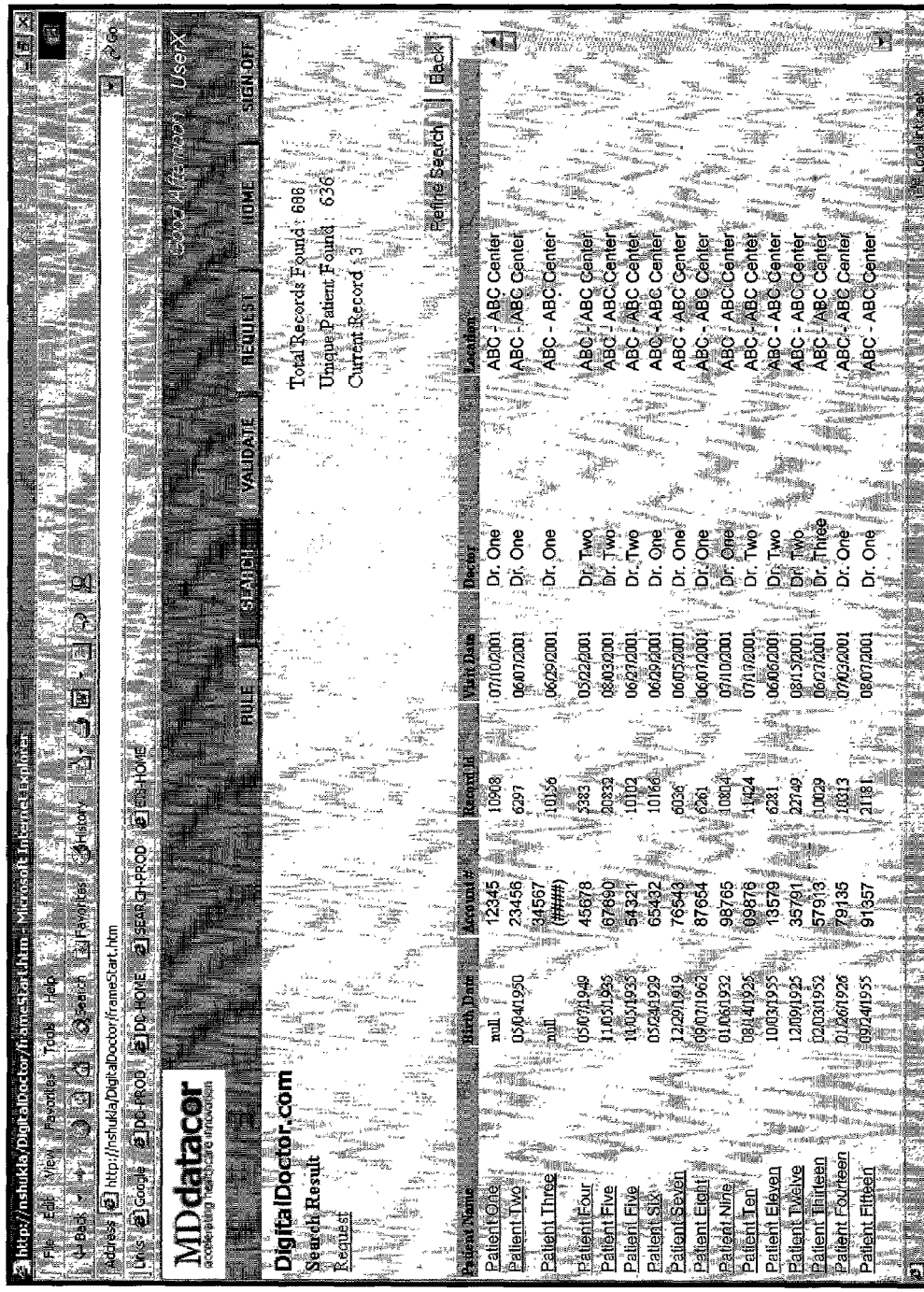
Figure 14C:
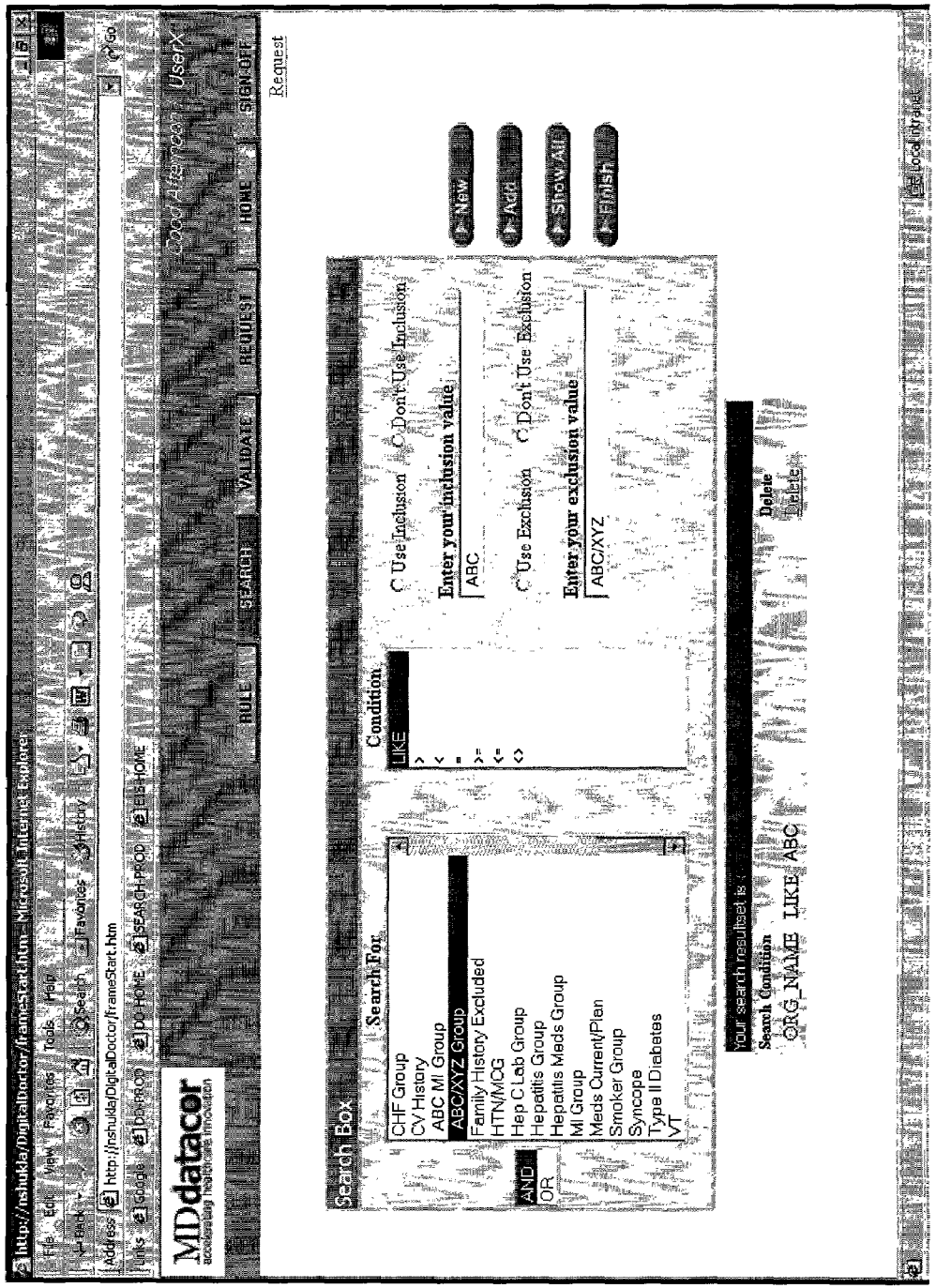
Figure 14D:
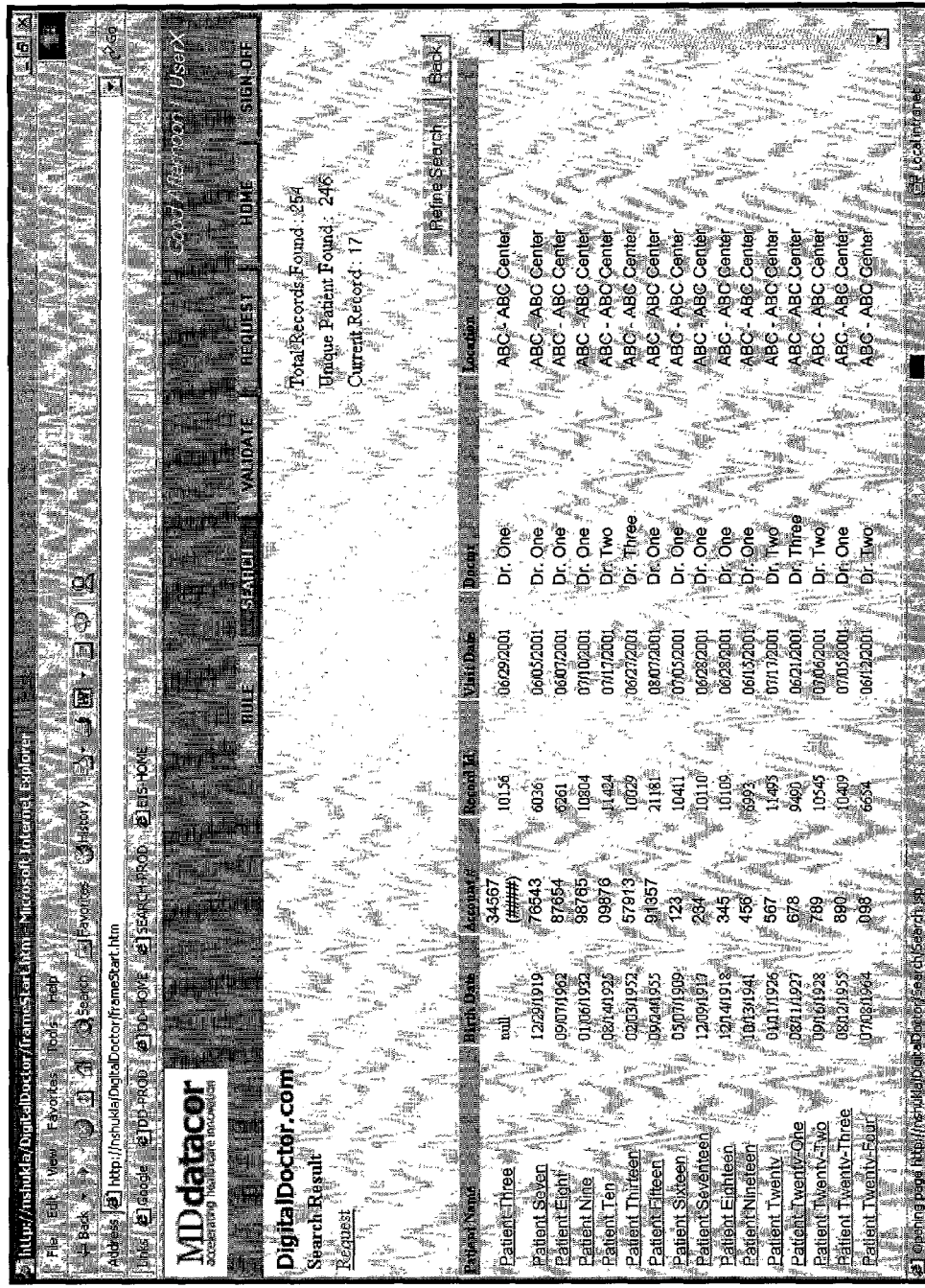
Figure 14E:
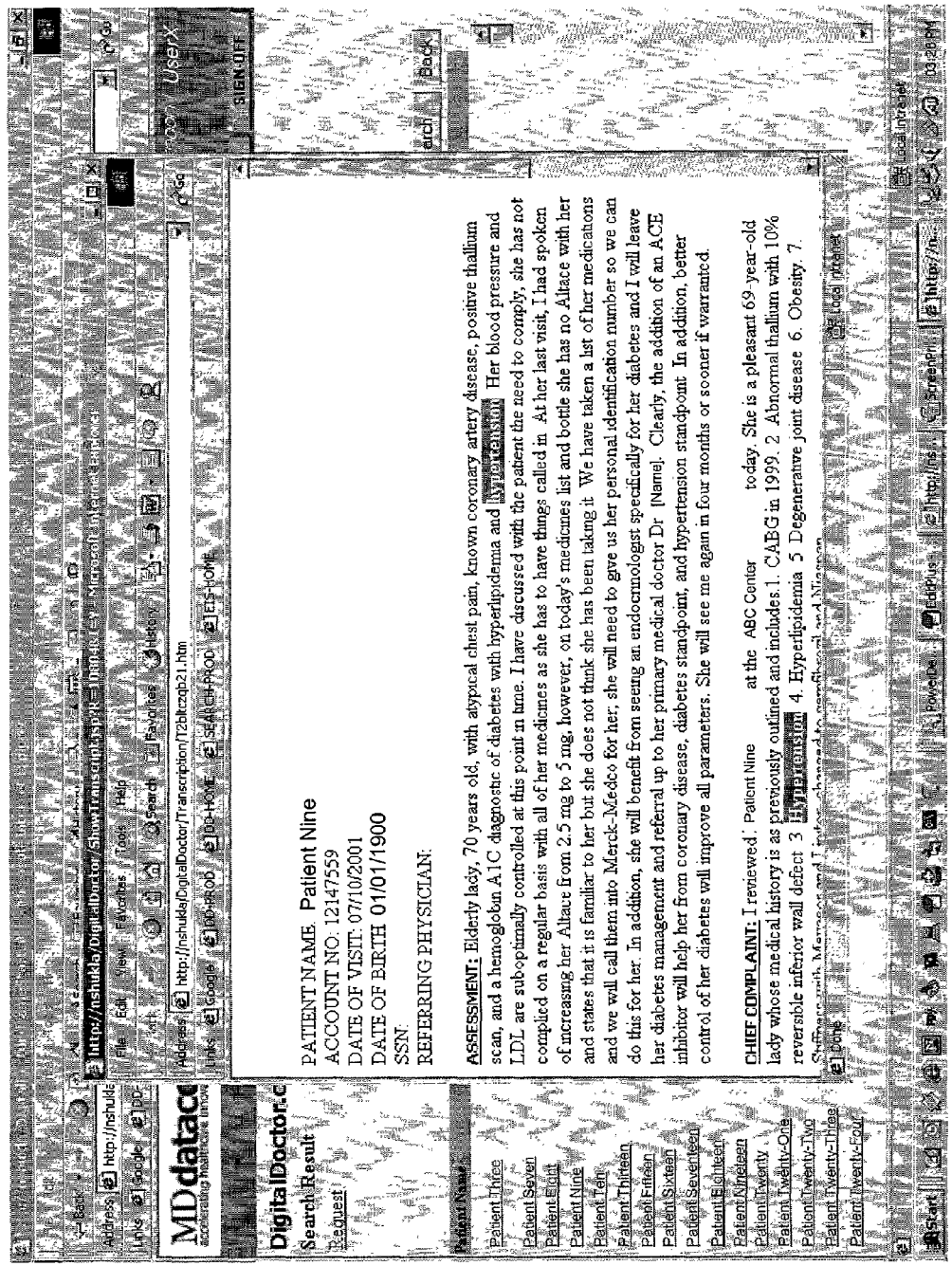
Figure 15A:
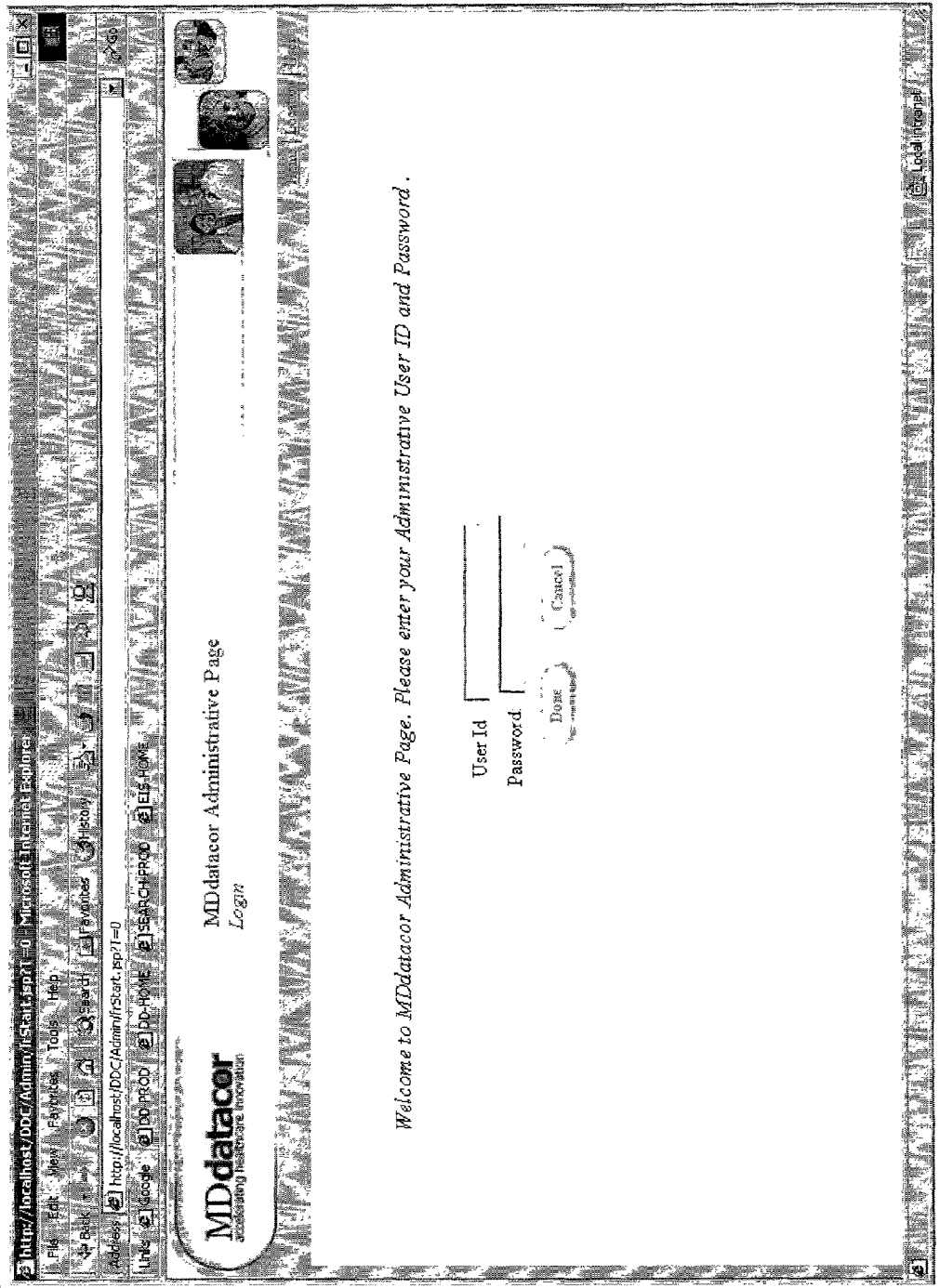
FIGS. 15A through 15E are sample screen snapshots that illustrate an administrative interface to the data warehouse system.
Figure 15B:
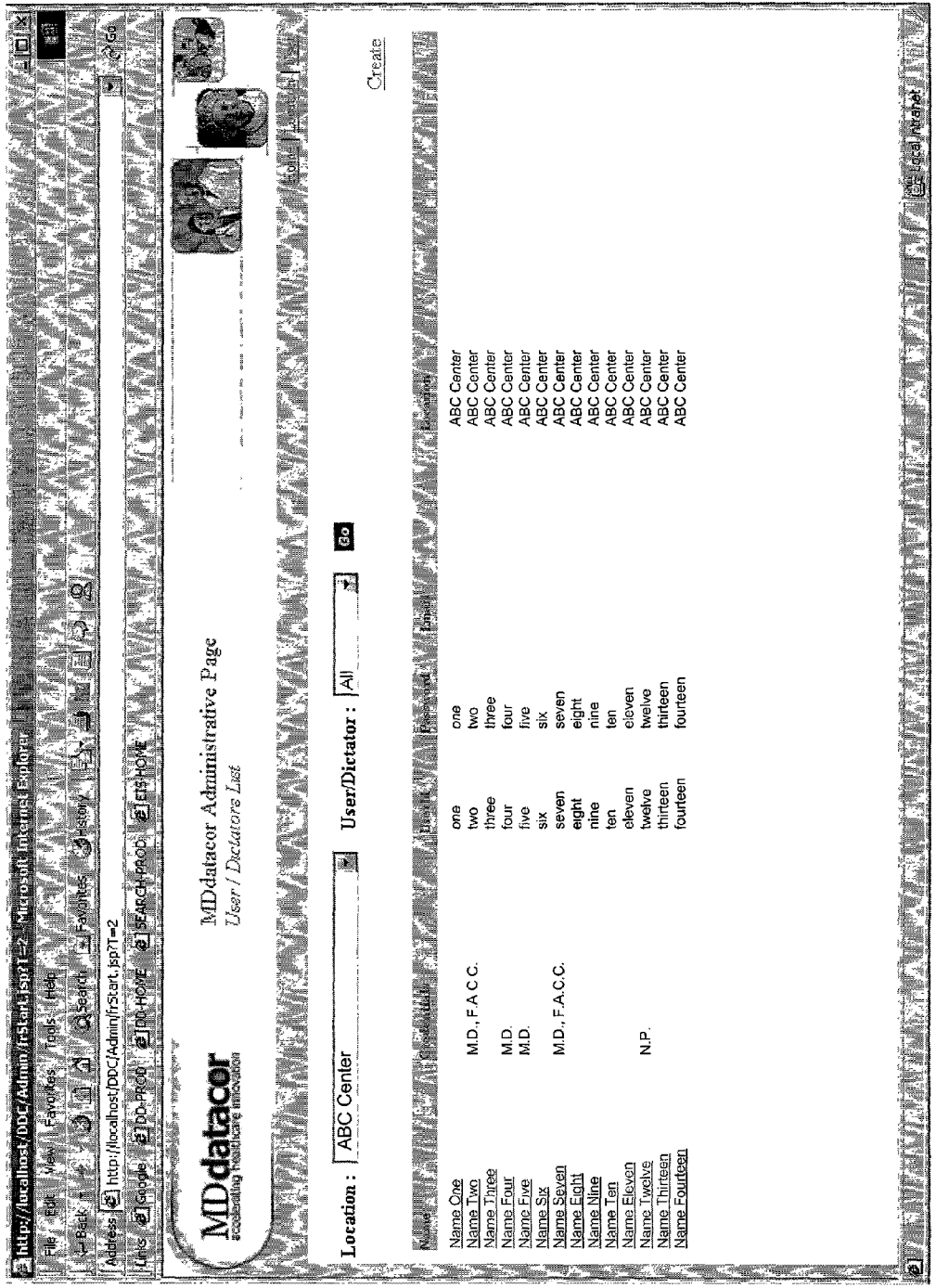
Figure 15C:
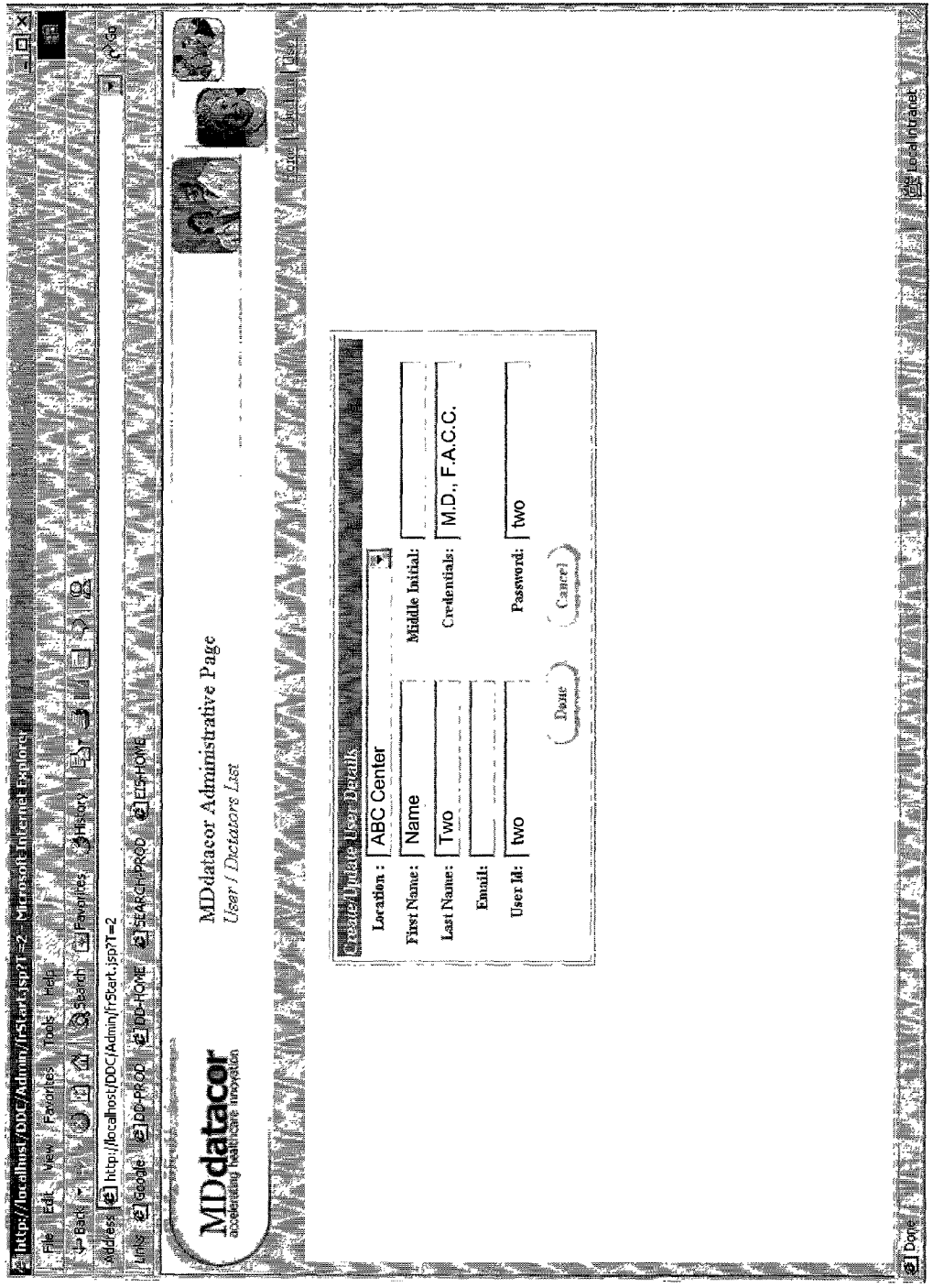
Figure 15D:
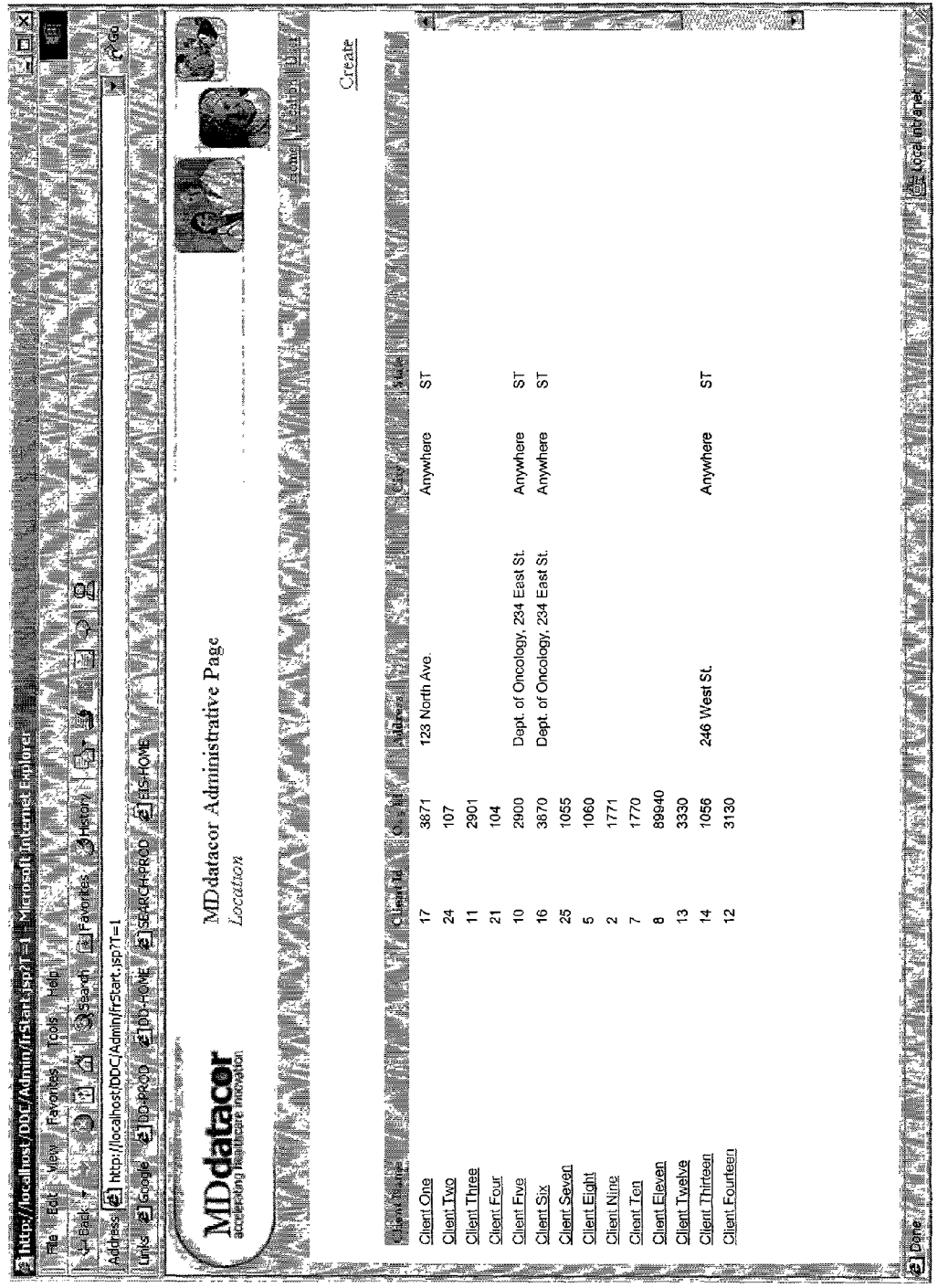
Figure 15E:
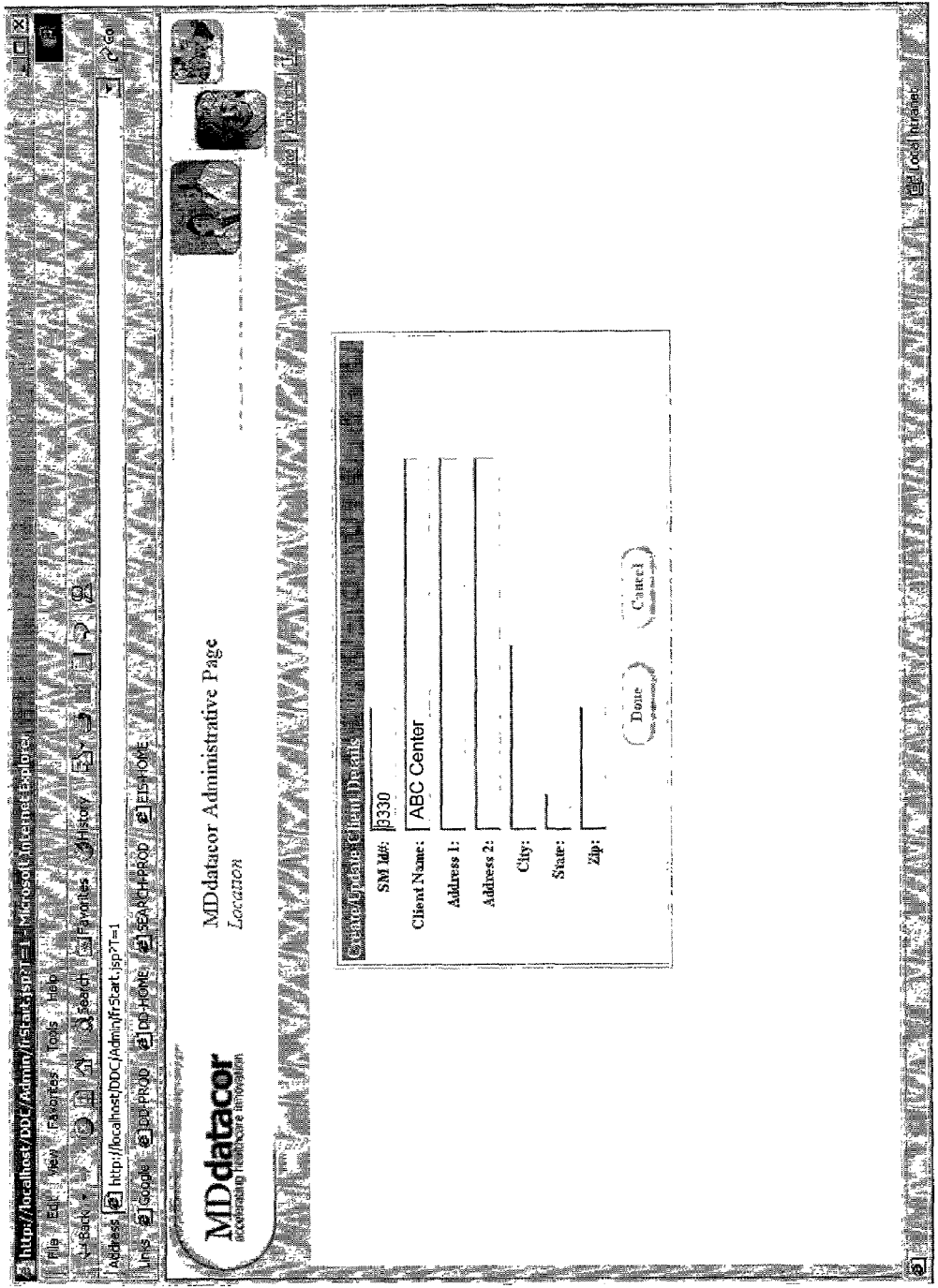

FIG. 11 illustrates a structure of clinical, diagnostic, and treatment data 332 shown in FIG. 3. Clinical, diagnostic, and treatment data 332 is a data warehouse that supports clinical or management decision making. The data that comprises clinical, diagnostic, and treatment data 332 is grouped into logical components of the data warehouse for specialty and demographics 1110, oncology 1120, urology 1130, cardiology 1140, gastroenterology 1150, and orthopedics 1160. In one embodiment, specialty and demographics 1110 has linked access to oncology 1120, urology 1130, cardiology 1140, gastroenterology 1150, and orthopedics 1160, and only specialty and demographics 1110 is externally accessible. In another embodiment, each logical component is separate, not linked to any other logical component, and externally accessible.

Although the embodiments disclosed herein describe a fully functioning system, method, and apparatus for storing and retrieving clinical, diagnostic, and treatment data in a natural human language format, the reader should understand that other equivalent embodiments exist. Since numerous modifications and variations will occur to those who review this disclosure, the system, method, and apparatus for storing and retrieving clinical, diagnostic, and treatment data is not limited to the exact construction and operation illustrated and disclosed herein. Accordingly, this disclosure intends all suitable modifications and equivalents to fall within the scope of the claims.

EXAMPLES

Example 1

Lone QT Syndrone

A physician enters the following clinical information into a system for determining a patient's disease risk or susceptibility type and/or drug response polymorphism:

A 42-year-old patient has a family history of cardiac arrest in one first and one second degree relative. Patient has had an occasional syncopal episode. His clinical evaluation is normal. His EKG is normal apart from slight lengthening of his QT interval. Patient takes an antihistamine for seasonal allergies.

The system notifies the physician that the patient may have partially penetrant Long QT syndrome. Genetic testing is recommended and the patient undergoes genetic testing for one of the 5 genes associated with Long QT syndrome. The patient is found to have a mutation in LQT2, which effects potassium channels. The system recommends avoidance of all drugs that prolong cardiac repolarization such as antiarrythmics, gastrokinetics, antipsychotics, antihistamines and certain antibacterials. An alternative drug for his seasonal allergies is recommended. The system recommends further testing of the patients relatives. One sibling and one daughter are found to have the same LQT2 mutation. Physician makes recommendations to patient and family members about avoidance of above mentioned drugs to avoid sudden cardiac deaths.

Example 2

Arthritis and Anemia—Thiopurine S-Methyltransferase Mutation

A physician enters the following clinical information into a system for determining a patient's disease risk or susceptibility type and/or drug response polymorphism:

A 70-year-old woman has been placed on azathioprine for arthritis by her GP. Three months after beginning treatment her doctor notes that she is anemic. Work up for GI bleeding is negative.

The system generates a result set that includes a suggestion to the physician to test the patient for a mutation in her Thiopurine S-Methyltransferase (TPMT) Gene Locus. The patient is found to be heterozygous for mutant TPMT which results in severe hematopoietic toxicity and resultant anemia. The system generates a result set that includes a suggestion to the physician that the patient has a genetic polymorphism, which makes her intolerant to thiopurine medications, and suggest alternative non-TPMT metabolized anti-arthritic medication.

Example 3

Colonic Neoplasia and Rapid Metabolic Phenotype for Acetyltransferase and Cytochrome P4501A2

A physician enters the following clinical information into a system for determining a patient's disease risk or susceptibility type and/or drug response polymorphism:

A 50-year-old male patient undergoes screening colonoscopy. The patient has a family history of colon cancer. Dietary history records that he consumes red meat at almost every meal. He is found to have eight polyps, which are removed. In view of his polyps and family history his gastroenterologist recommends yearly colonoscopy. The system generates a result set that includes a suggestion to the physician to test for polymorphisms in N-acetyltransferase-2 (NAT2) and hepatic cytochrome P4501A2 (CYP1A2). Patient is found to have polymorphism in both genes resulting in the patient being a rapid metabolizer of heterocyclic amines. Heterocyclic amines are found in over cooked red meat. Rapid metabolizers of heterocyclic amines produce chemical carcinogens, which may increase the risk of colon cancer. The system generates a result set that includes a suggestion to the physician of his patient's fast acetylator status and to reduce his meat consumption. The system also generates a result set that includes a suggestion to the physician to investigate a new cancer preventative agent designed for fast acetylators.

There is increasing evidence from epidemiologic studies that fast acetylators who consume overly cooked red meat may be at increased risk for colon cancer. This kind of susceptibility testing will assume increasing importance. The system will prompt physicians to perform genetic testing when indicated. The average physician is unlikely to be aware of what the latest recommendations are, particularly as most do not follow the latest advances in the relationship between genetic/molecular biology and clinical medicine.

Example 4

Breast Cancer BRCA1/2 Mutations and Estrogen Metabolism

A physician enters the following clinical information into a system for determining a patient's disease risk or susceptibility type and/or drug response polymorphism:

A 35-year-old woman has a family history of one first degree and one second degree relative with premenopausal breast cancer. Patient has had a previous benign breast biopsy, which demonstrated atypical ductal hyperplasia. The patient's menarche was at the age of 12 and she has no children. The system automatically calculates the patient's risk of breast cancer and inform her physician that she has a 5.2 times higher risk than the normal population and that she should undergo BRCA1 testing and BRCA2 testing. Testing is performed by Myriad genetics and the results are negative (Negative BRCA1 and BRCA2 does not guarantee that a patient will not develop breast cancer, only that they do not have one of the known familial types).

The system generates a result set that includes a suggestion to the physician that the patient is tested for one of the known polymorphisms affecting estrogen metabolism. Estradiol (E2) the active form of estrogen can be metabolized by 17β-hydroxysteroid dehydrogenase (17β-HSD) to estrone (E1). The 16α-hydroxylation of E1 and E2 is performed by cytochrome P450 (CYPs), CYP3A4 and CYP2C9. 16αHE1 may be increased in breast tissues of patients who develop breast cancer. Alternatively E2 may be metabolized from hydroxylation of the aromatic A ring to 2,3 and 3,4-catechol estrogens which is mediated by several P450 isoforms including CYP1A1, CYP1A2 and CYP3A4. Increased formation of catechol estrogen has also been implicated as a factor in breast cancer. The metabolism of catechol estrogens is regulated by the action catechol O-methyl transferases (COMTs). COMT is polymorphic with 25% of the Caucasian population homozygous for a low activity allele ($COMT^{Met/Met}$). Epidemiological studies have demonstrated an increased risk of breast cancer in patients with the low activity allele. Therefore estrogen metabolism may be altered in patients at increased risk for breast cancer with polymorphisms that result in:

Lower levels of the "good-estrogen" 17β-HSD;
Higher levels of the "bad-estrogens" 16αHE1 and catechol estrogens; and
Failure to detoxify the "bad-estrogens" such as the low activity allele ($COMT^{Met/Met}$).

The system will recommend genetic testing to identify patients at risk for breast cancer based on abnormal metabolism of estrogen (although this is not yet proven, it is the subject of intensive research and will likely become the standard of care in the future). Alternatively the system may recommend phenotype testing i.e., identify patients with abnormal serum, urinary or tissue levels of estrogen metabolites base on the individual patient's clinical profile. In addition, data suggesting proteonomics, functional genomics and biochemical testing recommendations should be made.

Once the abnormality in estrogen metabolism has been identified the system would suggest the prescription of particular SERM (selective estrogen receptor modulator) or specific drug affecting the down or up-regulated metabolic pathway, altered by the polymorphism.

Example 5

Coumadin and CYP2C9

A physician enters the following clinical information into a system for determining a patient's disease risk or susceptibility type and/or drug response polymorphism:

A 55-year-old patient has undergone recent coronary artery bypass surgery and has atrial fibrillation. He is started on coumadin as standard anticoagulation. His primary care physician admits him for control of his anticoagulation because he experiences recurrent bouts of epistaxis. The patient has to be admitted several times because he has an elevated INR and PT above the therapeutic range for coumadin.

The system generates a result set that includes a suggestion to the physician that the patient should be tested for a SNP in CYP2C9. The patient is found to have a polymorphism in CYP2C9 (one percent of the US population are poor metabolizers of coumadin and risk overdose and death). The system generates a result set that includes a suggestion to the physician that coumadin may be unsafe in this patient, and generates a result set that includes a suggestion to the physician that Plavix® is a safer alternative.

Example 6

Alzheimer's and Apolipoprotein E

A physician enters the following clinical information into a system for determining a patient's disease risk or susceptibility type and/or drug response polymorphism:

A neurologist places a 70-year-old patient with early Alzheimer's on Tacrine®. Her family reports after 3 months that the patient has continued to deteriorate and now does not recognize any one in the family.

The system generates a result set that includes a suggestion to the physician to test for the ApoE isoform 4 (ApoE-4). The patient tests positive for this polymorphism. The system generates a result set that includes a suggestion to the physician to consider stopping the drug and trying an alternative. Patients with the ApoE-4 genotype do not respond to Tacrine®.

Example 7

Prostate Cancer Risk and Glutathione S-Transferase P1 Polymorphisms

A physician enters the following clinical information into a system for determining a patient's disease risk or susceptibility type and/or drug response polymorphism:

A 50-year-old male with a no family history of prostate cancer has a borderline PSA of 7.5 on routine screening. Digital rectal examination and ultrasound examination of the prostate are normal.

The system generates a result set that includes a suggestion to the physician to test the patient for a glutathione S-transferase P1 polymorphism which has recently been shown to correlate with an increased risk of prostate cancer. Glutathione S-transferase (GST) has been implicated in the metabolism and detoxification of carcinogens and it is thought that the marked inter-racial variation in prostate cancer risk may be related to polymorphic variation in detoxification of carcinogens. The patient tests positive for a GSTP1 polymorphism and the system recommends that the patient be prescribed Proscar® (finasteride) which selectively inhibits 5α-reductase and inhibits the conversion of testosterone to its active form 5α-DHT and may prevent prostate cancer.

GST polymorphisms have not been established as a definite risk factor for prostate cancer, and Proscar®'s role in prevention has also not yet been established. Both are pending the results of a major clinical trial yet to be announced. However, this is likely the way medicine will be practiced in the future.

Example 8

Colon Cancer Treatment and Neurotoxicity Associated with Dihydropyrimidine Dehydrogenase (DPD) Deficiency A physician enters the following clinical information into a system for determining a patient's disease risk or susceptibility type and/or drug response polymorphism:

A 72-year-old female has recently undergone a resection of a colon cancer. She had a Dukes Stage C and elects to receive standard chemotherapy with 5-fluorouracil and leucovorin. The patient develops ringing in her ears and some numbness. This is a rare complication on this drug regimen.

The system generates a result set that includes a suggestion to the physician to test the patient for DPD deficiency due to a polymorphism for this enzyme. The patient tests positive. The system generates a result set that includes a suggestion to the physician that her neurotoxicity may be due to rare DPD deficiency and her 5FU should be stopped. The system generates a result set that includes a suggestion to the physician that the patient be placed on an alternative regimen consisting of CPT-11.

Example 9

Asthma and Polymorphisms in the β2-ADRENOCEPTOR

A physician enters the following clinical information into a system for determining a patient's disease risk or susceptibility type and/or drug response polymorphism:

A 10-year-old boy has been under the care of his physician and standard doses with a β2-agonists are ineffective in controlling his recurrent bouts of asthma.

The system informs the physician that the boy may have a polymorphism in the β2-adrenoceptor. The system recommends genetic testing which is positive. The system recommends an inhalational glucocorticoid that does not work through the β2-adrenoceptor, and his symptoms improve.

Example 10

Depression and CYP2D6

A physician enters the following clinical information into a system for determining a patient's disease risk or susceptibility type and/or drug response polymorphism:

A 45-year-old woman is placed on a tricyclic antidepressant, Elavil, by her family physician because of mood swings and depression. He notes that she is complaining of constipation and dizziness after only 2 weeks on the drug and doubles the dosage.

The system generates a result set that includes a suggestion to the physician that she should be tested for CYP2D6 polymorphisms because tricyclics are metabolized by this P450 enzyme. The patient tests positive for the CYP2D6*10 allelic variant which results in poor drug metabolism. The physician was planning to switch her to Prozac (a selective serotonin reuptake inhibitor). The system points out that even though Prozac is a different class of antidepressant it is also metabolized by CYP2D6 and that the patient should be prescribed a monoamine oxidase inhibitor.

The above example demonstrates that the system can generate a result set that includes treatment recommendations, thereby potentially preventing serious drug side effects or death.

Example 11

Hypertension and CYP2D6

A physician enters the following clinical information into a system for determining a patient's disease risk or susceptibility type and/or drug response polymorphism:

A 50-year-old man was placed on a betablocker for hypertension, and has been experiencing dizziness and fainting after two weeks on treatment.

The system notifies the cardiologist that the patient should undergo genetic testing for CYP2D6, a cytochrome p450 metabolizing enzyme SNP. The system generates a result set that includes a suggestion to the physician to consider testing by Affymetrix and the test is positive. The patient is identified with a hypertension drug response polymorphism. The system generates a result set that includes a suggestion to the physician to consider an alternative drug not metabolized by p450.

Example 12

Identification of Germ Line Mutations—Cystic Fibrosis and the Role of Modifier Genes The gene responsible for cystic fibrosis was identified in 1989. Cystic fibrosis has often been described as a classic Mendelian disorder, which means if one inherited the gene and its mutation one would get the disease. However, it has become apparent that "single disease genes" probably do not exist, and that "modifier genes" play a significant role in the severity of a disease. For example, in the case of cystic fibrosis, patients with identical mutations in the cystic fibrosis gene vary substantially in the severity of the diseases. Some cystic fibrosis patients develop recurrent bouts of lung infection, while others with the same mutation show no signs of problems. Those with the most severe form die in the first few years of life from pneumonia. Variations in male infertility and pancreatitis (other components of cystic fibrosis) have been reported despite patients having the same mutation. Environmental factors play a part in phenotypic variation, but so do "modifier genes" and SNPs. Some researchers have described the cystic fibrosis transmembrane conductor regulator (CFTR), the protein produced by the cystic fibrosis gene, as a complex network much like the Internet. The CTFR has nodes connected around it. It is largely tolerant of failure, unless a key "node" or modifying protein fails. Some of these modifier genes and their proteins are thought to have loci that correspond to inflammatory proteins like TNF-alpha. Thus, without being bound by theory, it is possible that the patients with the most severe form of respiratory problems due to cystic fibrosis have increased inflammatory proteins because of a modifier gene producing an inflammatory protein.

Therefore, integration of detailed clinical information with genetic information is critical to provide more accurate prognostic or predictive information that yields a truer estimation of a patient's disease or risk along a gradient of disease severity. For example, a physician enters the following clinical information into the system of the invention:

A child with recurrent bouts of upper respiratory tract infection that respond to antibiotics.

The system notifies the treating physician that genetic testing for cystic fibrosis should be considered, and based upon the patient's response to treatment, the system may provide suggestions for testing for modifier genes or SNPs (genomic testing), or for the presence of inflammatory proteins (proteonomic testing). If inflammatory proteins are present, the system may provide the treating physician with a suggestion of an anti-inflammatory drug which improves the outcome for the patient. The system may also suggest the appropriate modifier gene testing required to give a more accurate prognosis, as well as prophylactic treatments based upon the presence or absence of modifier genes. In addition, system may notify the physician of other pharmaceutical companies that may be developing drugs that inhibit the inflammatory proteins produced by the modifier genes.

Example 13

Somatic Testing of Tumor Samples—Colorectal Cancer and Thymidylate Synthase Expression The testing of colorectal tumor specimens for thymidylate synthase (TS) expression in colorectal cancer has been shown to predict the clinical response to 5-fluorouracil (a drug used in the treatment of colorectal cancer). Response rates are reported higher than 71% in patients with low TS in metastatic tumur samples, and as low as 20% in patients with high TS activity in metastatic tumor samples. A pathology laboratory may recommend this type of tumor sample testing to a physician in patients not responding to standard chemotherapy for colorectal cancer once clinical information demonstrating non-response is obtained from the database system of the invention. The pathology laboratory may test tumor samples sent by the physician for somatic mutations in the samples. Genomic testing of a blood sample for a polymorphism in TS metabolism could also be recommended in the appropriate clinical context, as this particular germ-line mutation may also influence the tumor response to a drug.

For patients who do not respond to traditional therapy, the database system would identify appropriate testing based on disease severity and treatment response gradients. This is a much more cost effective way to implement genetic testing. The disease severity and treatment response gradients will be initially identified by the database system, and the information can then be provided to pathology, drug, or genomic companies.

We claim:

1. A method of querying a computer database that comprises a plurality of electronic data records containing strings of terms in a natural human language format, to retrieve a final result set comprising a selection of data records that satisfy a search query, comprising the steps of:

receiving input from a user corresponding to a creation of at least one initial inclusion rule, the initial inclusion rule comprising one or more descriptive search terms that are required to occur in each record in the final result set;

receiving input from a user corresponding to a creation of at least one initial exclusion rule, the initial exclusion rule comprising one or more descriptive search terms that are required to not occur in the final result set;

storing the at least one initial inclusion rule and the at least one initial exclusion rule as an initial descriptive taxonomy;

querying the computer database utilizing the initial descriptive taxonomy as a search query to generate an initial inclusion result set and an initial exclusion result set;

displaying the initial inclusion result set and the initial exclusion result set to the user, for inspection by the user to assess whether the initial inclusion result set and the initial exclusion result set comprise records desired by the user, the display of the initial inclusion result set including an exclusion flag identifying data records that also appear in the initial exclusion result set;

receiving input from the user corresponding to a provision of additional descriptive search terms for addition to the descriptive search terms in the initial inclusion rule such that further data records containing such additional descriptive search terms will be included in the final result set;

storing the additional descriptive search terms for the initial inclusion rule as an updated inclusion rule;

receiving input from the user removing the exclusion flag for a particular data record that the user has determined should occur in the final result set notwithstanding its occurrence in the initial exclusion result set;

storing information relating to a data record for which an exclusion flag has been removed as an updated exclusion rule, such that the data record will henceforth occur in the final result set;

storing the updated inclusion rule and the updated exclusion rule as an updated descriptive taxonomy; and querying the computer database utilizing the updated descriptive taxonomy as a search query to generate the final result set, whereby data records that satisfy the updated inclusion rule are included in the data records in the final result set and data records for which the exclusion flag has been removed also are included in the final result set.

2. The method of claim 1, wherein the plurality of electronic data records comprise electronic medical records.

3. The method of claim 2, wherein the electronic medical records comprise heterogeneous data.

4. The method of claim 1, wherein the plurality of electronic data records comprise structured electronic medical records.

5. The method of claim 4, wherein the structured electronic medical records comprise heterogeneous data.

6. The method of claim 1, wherein the computer database is a data warehouse.

7. The method of claim 1, further comprising the step of displaying the final result set.

8. The method of claim 1, wherein the descriptive search terms include groups of clinical descriptions, the clinical descriptions having multiple related medical terms.

9. The method of claim 1, further comprising the step of selecting an initial descriptive taxonomy from a plurality of prestored initial descriptive taxonomies prior to the step of querying the computer database utilizing the initial descriptive taxonomy.

10. The method of claim 9, wherein storing the at least one inclusion rule and the at least one exclusion rule further comprises the step of combining the at least one initial inclusion rule with at least one existing inclusion rule from the selected initial descriptive taxonomy.

11. The method of claim 9, wherein storing the at least one inclusion rule and the at least one exclusion rule further comprises the step of combining the at least one initial exclusion rule with at least one existing exclusion rule from the selected initial descriptive taxonomy.

12. A system for querying a computer database that comprises a plurality of electronic data records containing strings of terms in a natural human language format, to retrieve a final result set comprising a selection of data records that satisfy a search query, the system comprising:

an inclusion module processor for receiving input from a user corresponding to a creation of at least one initial inclusion rule, the initial inclusion rule comprising one or more descriptive search terms that are required to occur in each record in the final result set;

an exclusion module processor for receiving input from a user corresponding to a creation of at least one initial exclusion rule, the initial exclusion rule comprising one or more descriptive search terms that are required to not occur in the final result set;

a taxonomy storage module processor for storing the at least one initial inclusion rule and the at least one initial exclusion rule as an initial descriptive taxonomy;

an initial query module processor for querying the computer database utilizing the initial descriptive taxonomy as a search query to generate an initial inclusion result set and an initial exclusion result set;

a display module processor for displaying the initial inclusion result set and the initial exclusion result set to the user, for inspection by the user to assess whether the initial inclusion result set and the initial exclusion result set comprise records desired by the user, the display of the initial inclusion result set including an exclusion flag identifying data records that also appear in the initial exclusion result set;

an update inclusion processor module for receiving input from the user corresponding to a provision of additional descriptive search terms for addition to the descriptive search terms in the initial inclusion rule such that further data records containing such additional descriptive search terms will be included in the final result set;

an update inclusion storage module for processor storing the additional descriptive search terms for the initial inclusion rule as an updated inclusion rule;

an update exclusion module processor for receiving input from the user removing the exclusion flag for a particular data record that the user has determined should occur in the final result set notwithstanding its occurrence in the initial exclusion result set;

an update exclusion storage module processor for storing information relating to a data record for which an exclusion flag has been removed as an updated exclusion rule, such that the data record will henceforth occur in the final result set;

an update taxonomy storage module processor for storing the updated inclusion rule and the updated exclusion rule as an updated descriptive taxonomy; and a final query module processor for querying the computer database utilizing the updated descriptive taxonomy as a search query to generate the final result set, whereby data records that satisfy the updated inclusion rule are included in the data records in the final result set and data records for which the exclusion flag has been removed also are included in the final result set.

13. The system of claim 12, wherein the plurality of electronic data records comprise electronic medical records.

14. The system of claim 13, wherein the electronic medical records comprise heterogeneous data.

15. The system of claim 12, wherein the plurality of electronic data records comprise structured electronic medical records.

16. The system of claim 15, wherein the structured electronic medical records comprise heterogeneous data.

17. The system of claim 12, wherein the computer database is a data warehouse.

18. The system of claim 12, further comprising a result display module for displaying the final result set.

19. The system of claim 12, wherein the descriptive search terms include groups of clinical descriptions, the clinical descriptions having multiple related medical terms.

20. The system of claim 12, further comprising a taxonomy selection module processor for selecting an initial descriptive taxonomy from a plurality of prestored initial descriptive taxonomies, wherein the selected initial descriptive taxonomy is utilized by the initial query module processor.

21. The system of claim 20, wherein the taxonomy storage module processor is further configured for combining the at least one initial inclusion rule with at least one existing inclusion rule from the selected initial descriptive taxonomy.

22. The system of claim 20, wherein the taxonomy storage module processor is further configured for combining the at least one initial exclusion rule with at least one existing exclusion rule from the selected initial descriptive taxonomy.

23. A computer-implemented method of querying a computer database that comprises a plurality of electronic data records containing strings of terms in a natural human language format, to retrieve a final result set comprising a selection of data records that satisfy a search query, comprising the computer-implemented steps of:

receiving input from a user corresponding to a creation of at least one initial inclusion rule, the initial inclusion rule comprising one or more descriptive search terms that are required to occur in each record in the final result set;

receiving input from a user corresponding to a creation of at least one initial exclusion rule, the initial exclusion rule comprising one or more descriptive search terms that are required to not occur in the final result set;

storing the at least one initial inclusion rule and the at least one initial exclusion rule as an initial descriptive taxonomy;

a computer querying the computer database utilizing the initial descriptive taxonomy as a search query to generate an initial inclusion result set and an initial exclusion result set;

displaying the initial inclusion result set and the initial exclusion result set to the user, for inspection by the user to assess whether the initial inclusion result set and the initial exclusion result set comprise records desired by the user, the display of the initial inclusion result set including an exclusion flag identifying data records that also appear in the initial exclusion result set;

receiving input from the user corresponding to a provision of additional descriptive search terms for addition to the descriptive search terms in the initial inclusion rule such that further data records containing such additional descriptive search terms will be included in the final result set;

storing the additional descriptive search terms for the initial inclusion rule as an updated inclusion rule;

receiving input from the user removing the exclusion flag for a particular data record that the user has determined should occur in the final result set notwithstanding its occurrence in the initial exclusion result set;

storing information relating to a data record for which an exclusion flag has been removed as an updated exclusion rule, such that the data record will henceforth occur in the final result set;

storing the updated inclusion rule and the updated exclusion rule as an updated descriptive taxonomy; and a computer querying the computer database utilizing the updated descriptive taxonomy as a search query to generate the final result set, whereby data records that satisfy the updated inclusion rule are included in the data records in the final result set and data records for which the exclusion flag has been removed also are included in the final result set.

24. The computer-implemented method of claim 23, wherein the plurality of electronic data records comprise electronic medical records.

25. The computer-implemented method of claim 24, wherein the electronic medical records comprise heterogeneous data.

26. The computer-implemented method of claim 23, wherein the plurality of electronic data records comprise structured electronic medical records.

27. The computer-implemented method of claim 26, wherein the structured electronic medical records comprise heterogeneous data.

28. The computer-implemented method of claim 23, wherein the computer database is a data warehouse.

29. The computer-implemented method of claim 23, further comprising the computer-implemented step of displaying the final result set.

30. The computer-implemented method of claim 23, wherein the descriptive search terms include groups of clinical descriptions, the clinical descriptions having multiple related medical terms.

31. The computer-implemented method of claim 23, further comprising the computer-implemented step of selecting an initial descriptive taxonomy from a plurality of prestored initial descriptive taxonomies prior to the step of the computer querying the computer database utilizing the initial descriptive taxonomy.

32. The computer-implemented method of claim 31, wherein storing the at least one inclusion rule and the at least one exclusion rule further comprises the computer-implemented step of combining the at least one initial inclusion rule with at least one existing inclusion rule from the selected initial descriptive taxonomy.

33. The computer-implemented method of claim 31, wherein storing the at least one inclusion rule and the at least one exclusion rule further comprises the computer-implemented step of combining the at least one initial exclusion rule with at least one existing exclusion rule from the selected initial descriptive taxonomy.

* * * * *